(12) United States Patent
Kato et al.

(10) Patent No.: US 10,295,466 B2
(45) Date of Patent: *May 21, 2019

(54) FLUORESCENCE INTENSITY CORRECTING METHOD, FLUORESCENCE INTENSITY CALCULATING METHOD, AND FLUORESCENCE INTENSITY CALCULATING APPARATUS

(71) Applicant: Sony Corporation, Tokyo (JP)

(72) Inventors: Yasunobu Kato, Kanagawa (JP); Yoshitsugu Sakai, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/452,085

(22) Filed: Aug. 5, 2014

(65) Prior Publication Data
US 2014/0365159 A1   Dec. 11, 2014

Related U.S. Application Data

(63) Continuation of application No. 13/089,961, filed on Apr. 19, 2011, now Pat. No. 8,825,431.

(30) Foreign Application Priority Data

Apr. 28, 2010 (JP) ................. 2010-104566

(51) Int. Cl.
*G01N 21/64* (2006.01)

(52) U.S. Cl.
CPC . *G01N 21/6428* (2013.01); *G01N 2021/6421* (2013.01); *G01N 2021/6439* (2013.01)

(58) Field of Classification Search
CPC ........................................... G01N 23/00

USPC ......... 702/19, 20, 57, 66, 73, 107, 106, 179; 382/133; 422/82.08; 435/7.21; 436/518
See application file for complete search history.

(56) References Cited

U.S. PATENT DOCUMENTS 4,407,964 A * 10/1983 Elings et al. ................. 436/518
5,190,857 A *  3/1993 Allen et al. ................. 435/7.21
(Continued)

FOREIGN PATENT DOCUMENTS

CN       1711469       12/2005
JP       08-178849      7/1996
(Continued)

OTHER PUBLICATIONS

United States Court of Appeals for the Federal circuit, *Enfish* v *Microsoft*, decided May 12, 2016, pp. 1-30.*

(Continued)

*Primary Examiner* — Tung S Lau
(74) *Attorney, Agent, or Firm* — K&L Gates LLP

(57) ABSTRACT

A fluorescence intensity calculating apparatus, includes a measuring section configured to receive fluorescences generated from plural fluorescent dyes excited by radiating a light to a microparticle multiply-labeled with the plural fluorescent dyes having fluorescence wavelength bands overlapping one another by photodetectors which correspond to different received light wavelength bands, respectively, and whose number is larger than the number of fluorescent dyes, and obtain measured spectra by collecting detected values from the photodetectors, and a calculating section configured to approximate the measured spectra based on a linear sum of single-dyeing spectra obtained from the microparticle individually labeled with the fluorescent dyes, thereby calculating intensities of the fluorescences generated from the fluorescent dyes, respectively.

15 Claims, 39 Drawing Sheets

(56) References Cited

U.S. PATENT DOCUMENTS

| | | | |
|---|---|---|---|
| 5,922,285 A * | 7/1999 | Melendez et al. | 422/82.08 |
| 6,165,734 A * | 12/2000 | Garini et al. | 435/7.21 |
| 8,244,021 B2 | 8/2012 | Lett et al. | |
| 8,825,431 B2 * | 9/2014 | Kato et al. | 702/104 |
| 2003/0020908 A1 | 1/2003 | Frost et al. | |
| 2008/0018898 A1 | 1/2008 | Gunstream et al. | |
| 2008/0212866 A1 | 9/2008 | Lett et al. | |
| 2009/0128806 A1 | 5/2009 | Mimura et al. | |
| 2013/0323825 A1 * | 12/2013 | Sekino | G01N 21/6486 435/287.2 |

FOREIGN PATENT DOCUMENTS

| | | |
|---|---|---|
| JP | 2003-83894 | 3/2003 |
| JP | WO2007097171 | 8/2007 |
| WO | 97/22848 | 6/1997 |

OTHER PUBLICATIONS

Unites StatesCourt of Apeals for the Federal Circuit, *Electrical Power Group* v. *Alstom*, decided Aug. 1, 2016, pp. 1-12.*

European Office Action dated Sep. 18, 2014, for corresponding European Appln. No. 11003204.2.

Chinese Office Action dated Sep. 2, 2014, for corresponding Japanese Appln. No. 2011101011527.

Keenan et al., "Algorithms for Contrained Linear Unmixing with Application to the Hyperspectrcal Analysis of Fluorophore Mixtures", Imaging Spectometry, 2002, Proceedings of SPIE, vol. 4816, pp. 193-202.

Moore-Penrose pseudoinverse, Wikipedia, Sep. 11, 2014, pp. 1-8, XP_55139953A.

Chinese Office Action dated May 9, 2014 for corresponding Chinese Appln. No. 2011101011527.

Japanese Office Action dated Dec. 3, 2013, for corresponding Japanese Appln. No. 2010-104566.

Japanese Office Action dated Aug. 5, 2014, for corresponding Japanese Appln. No. 2010-104566.

Japanese Office Action dated Mar. 10, 2015, for corresponding Japanese Appln. No. 2010-104566.

European Communication dated Jun. 19, 2015, for corresponding European Appln. No. 11003204.2 (5 pages).

Japanese Office Action dated Aug. 11, 2015, for corresponding Japanese Appln. No. 2010-104566 (2 pages).

* cited by examiner

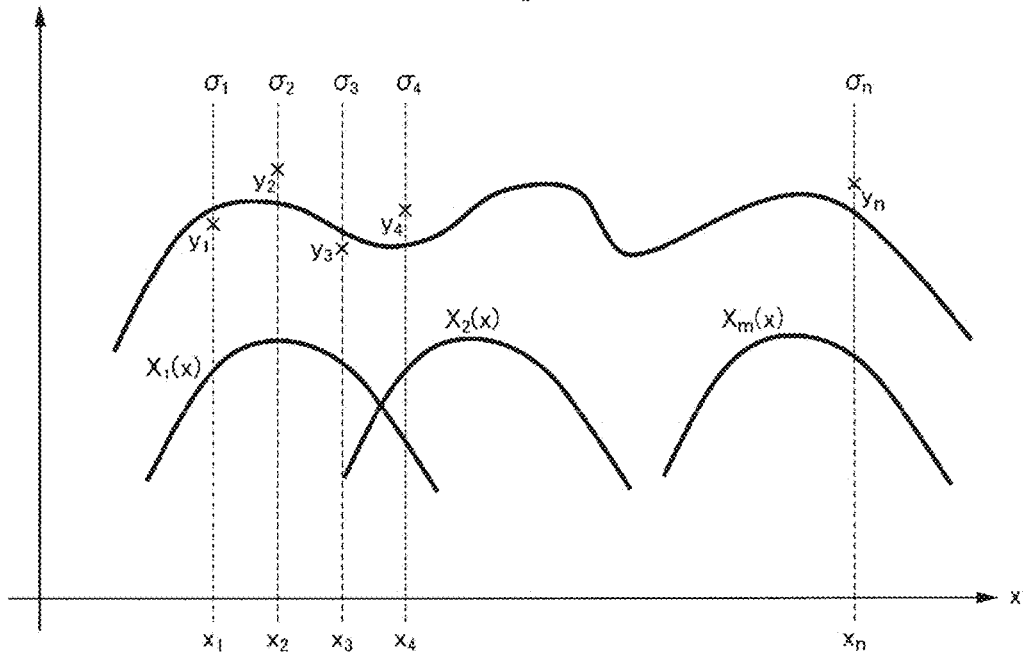

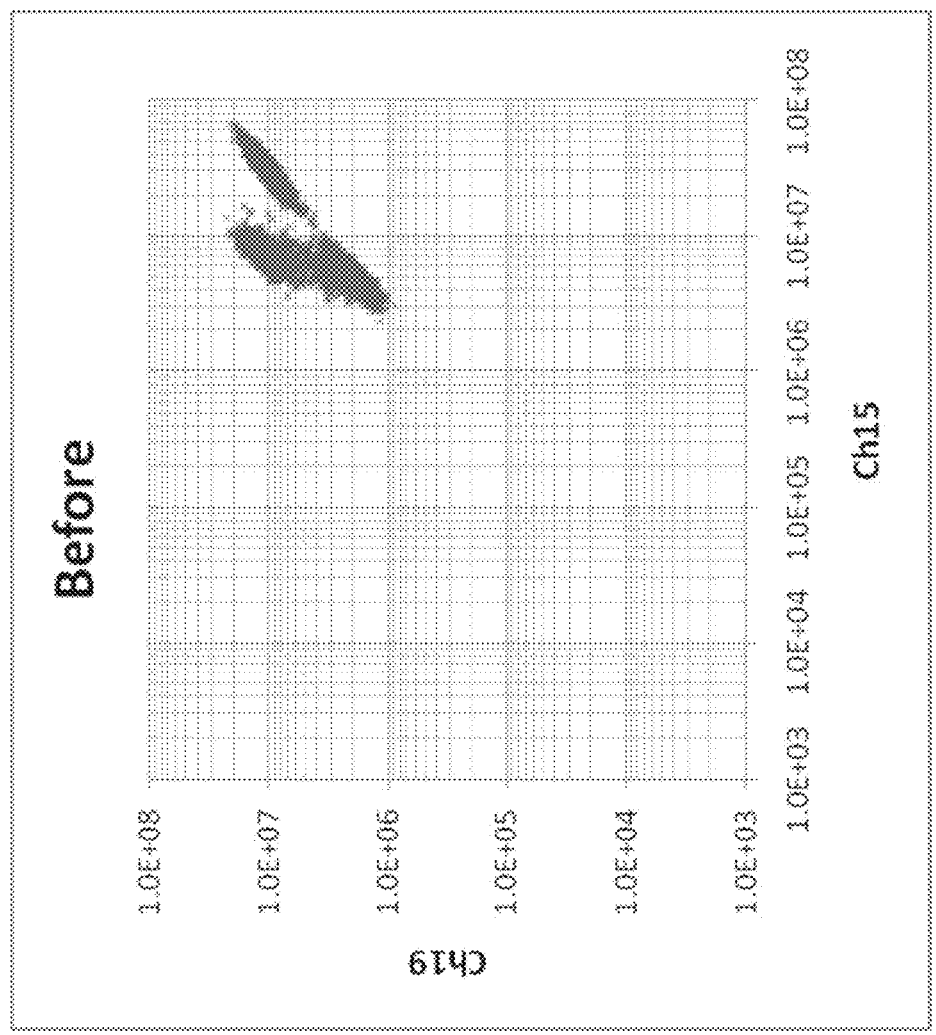

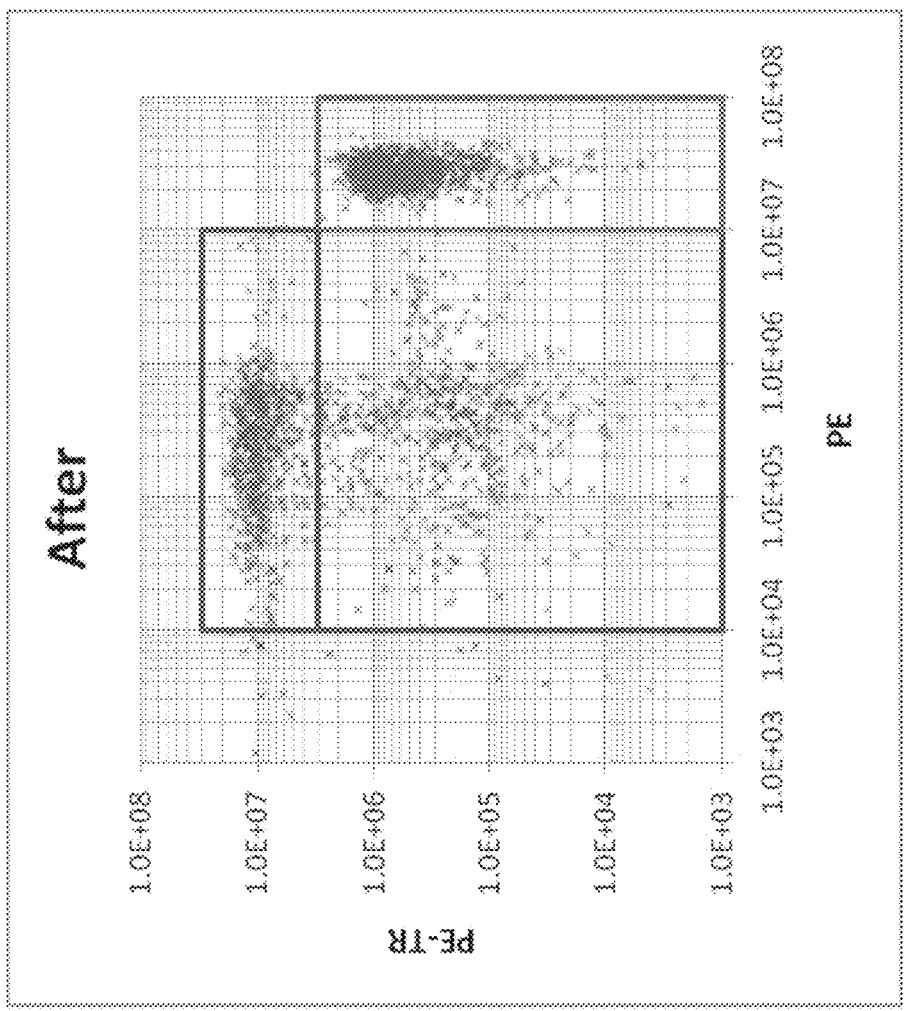

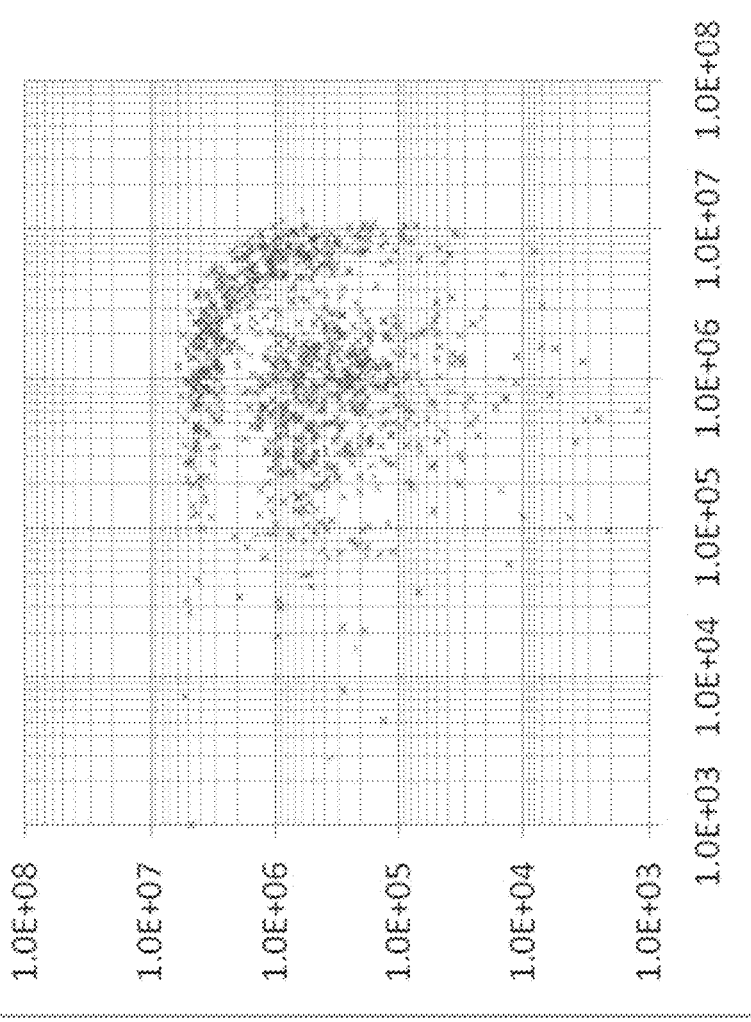

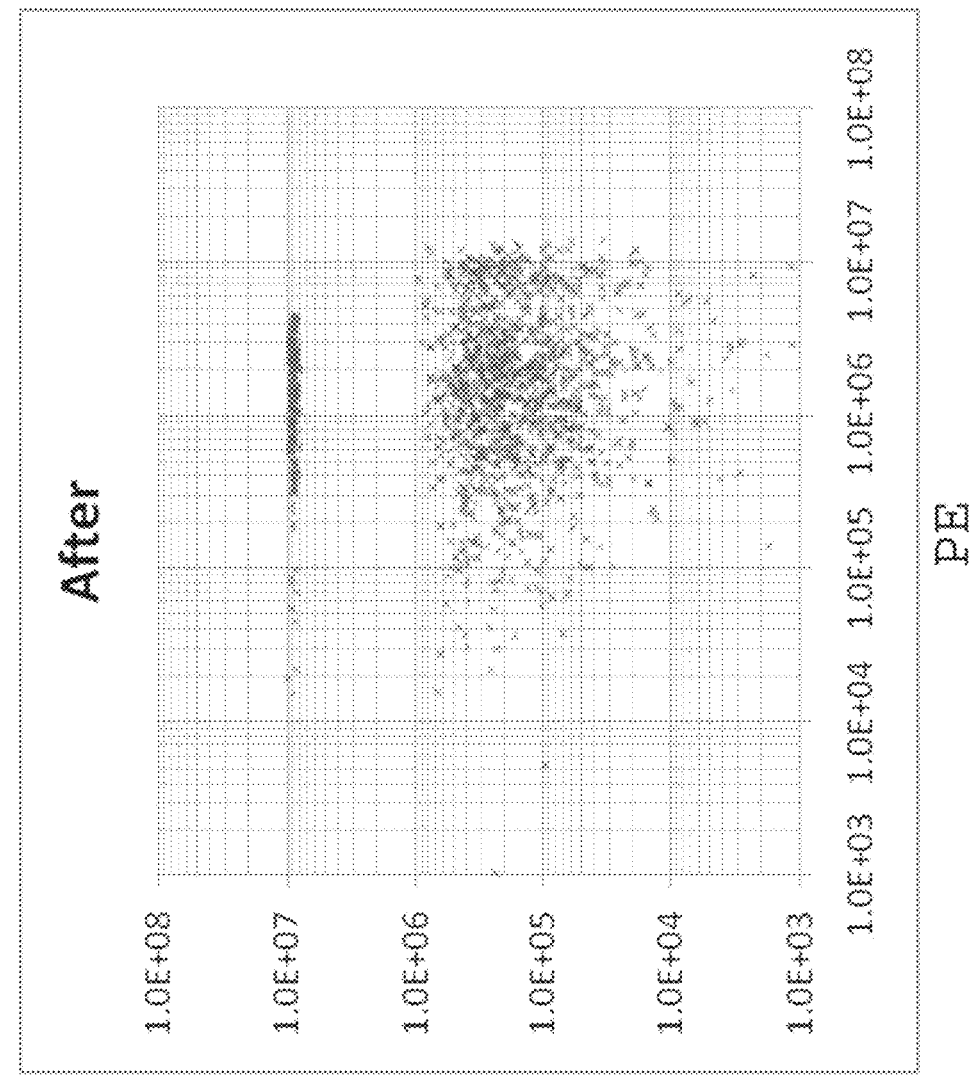

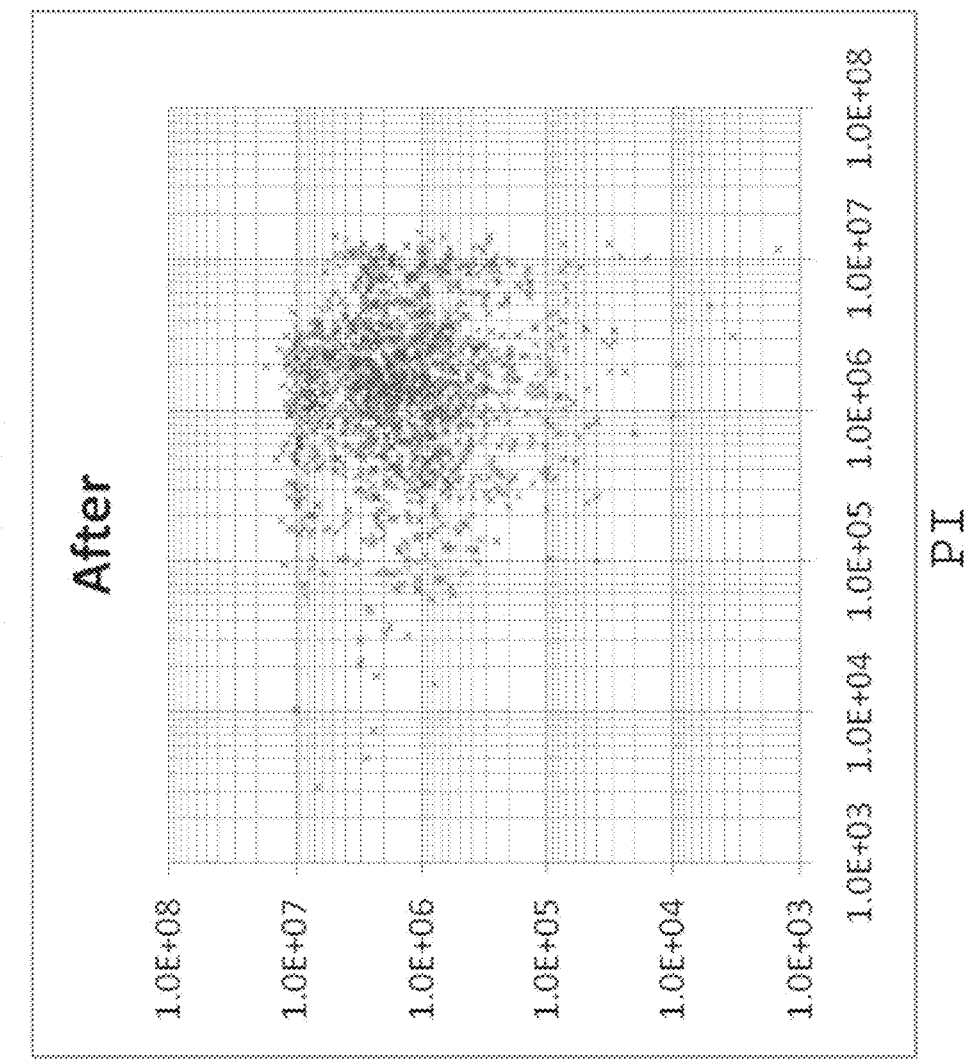

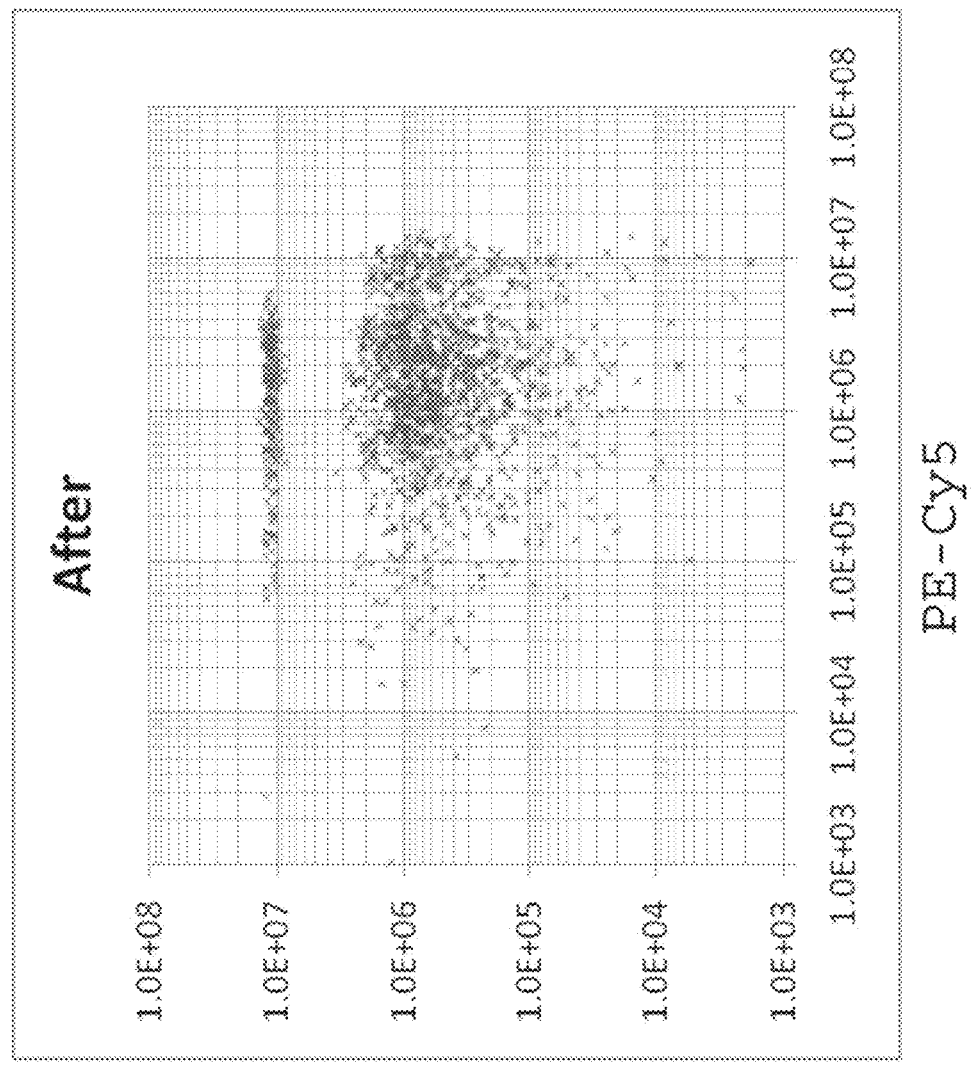

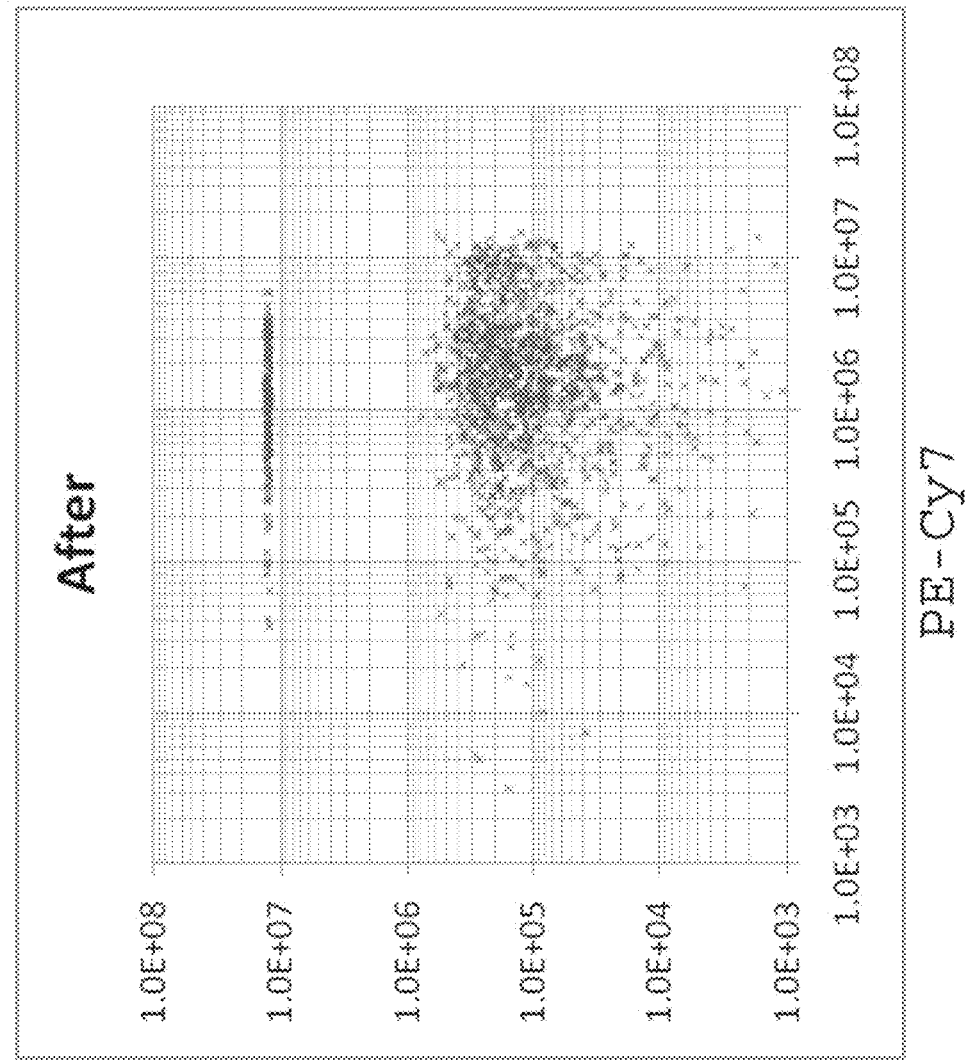

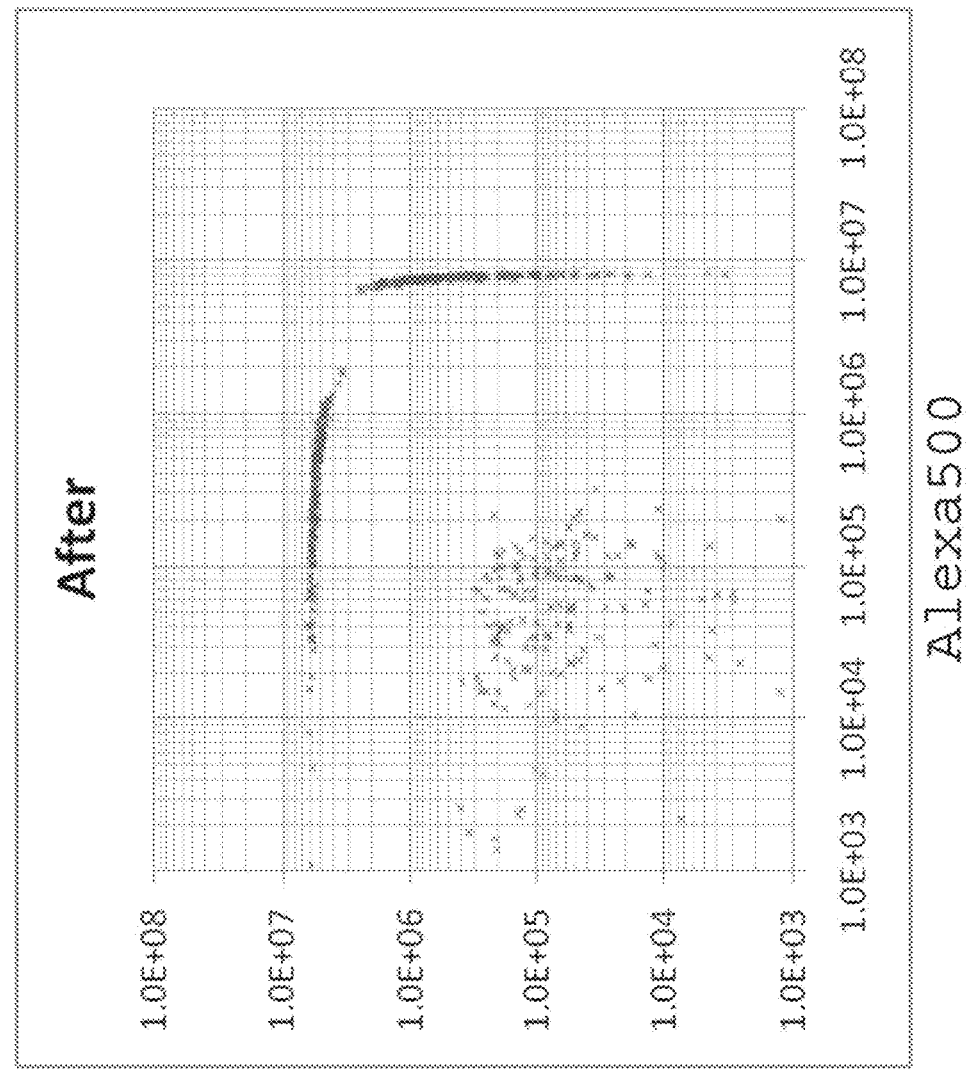

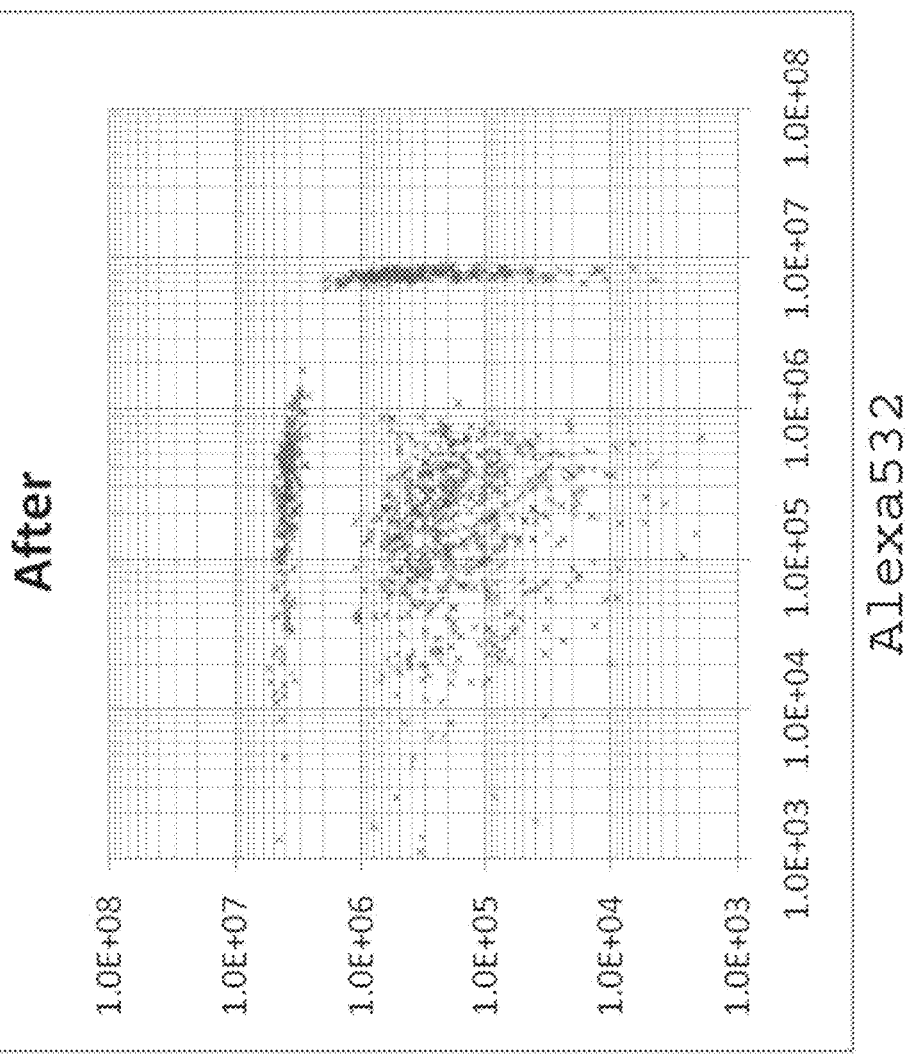

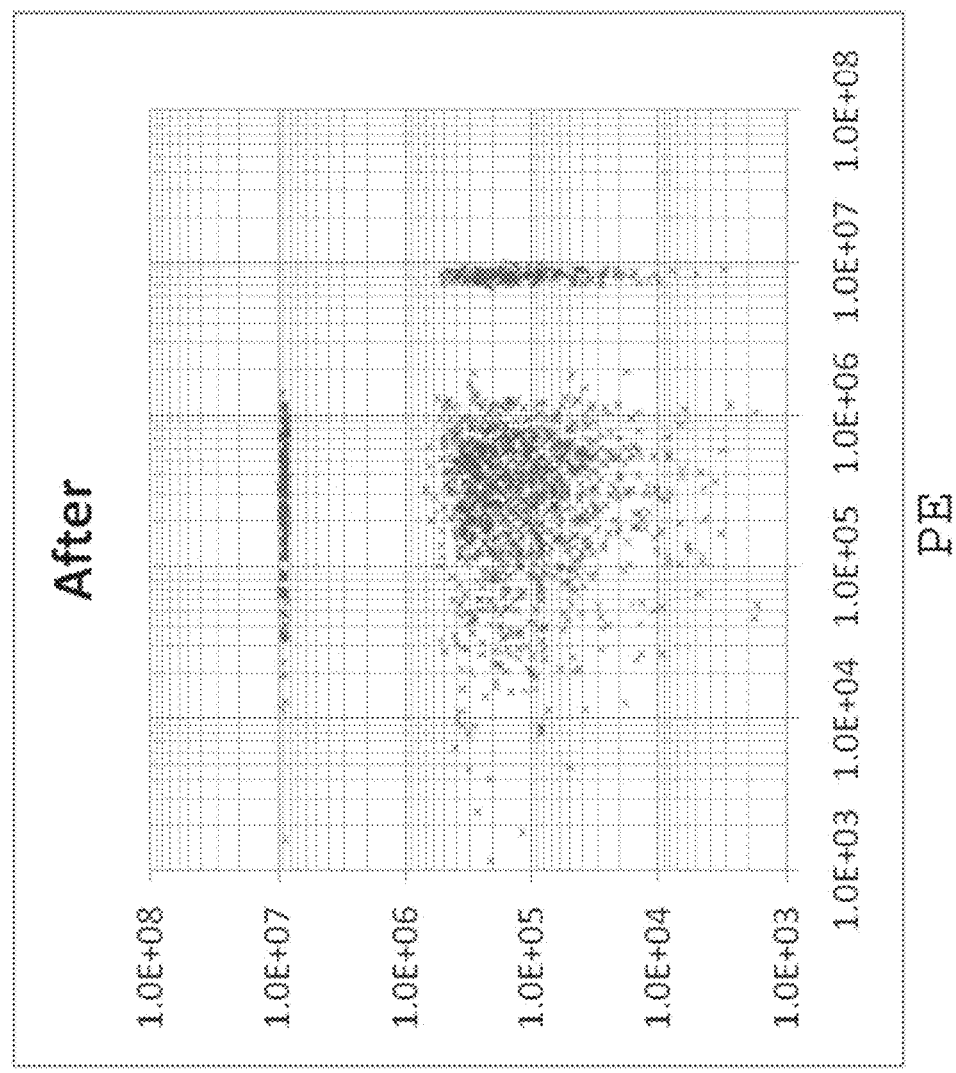

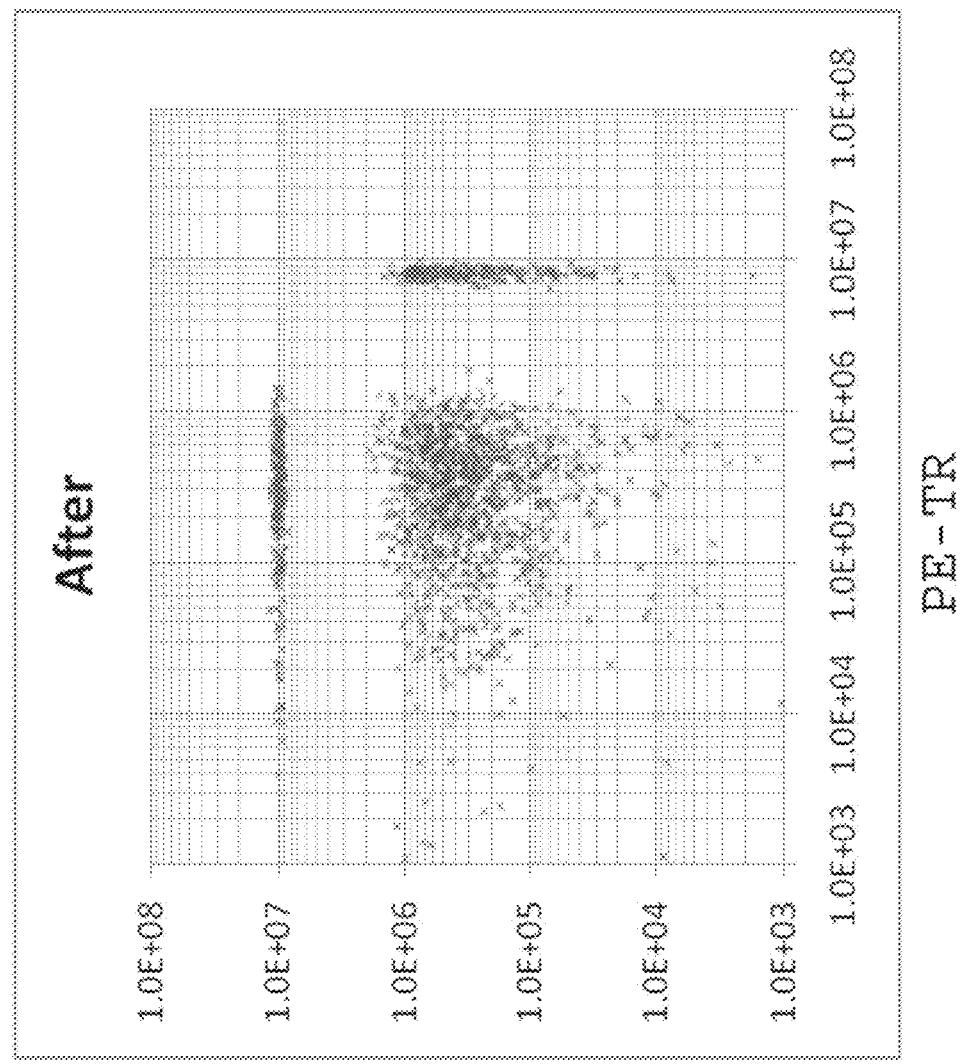

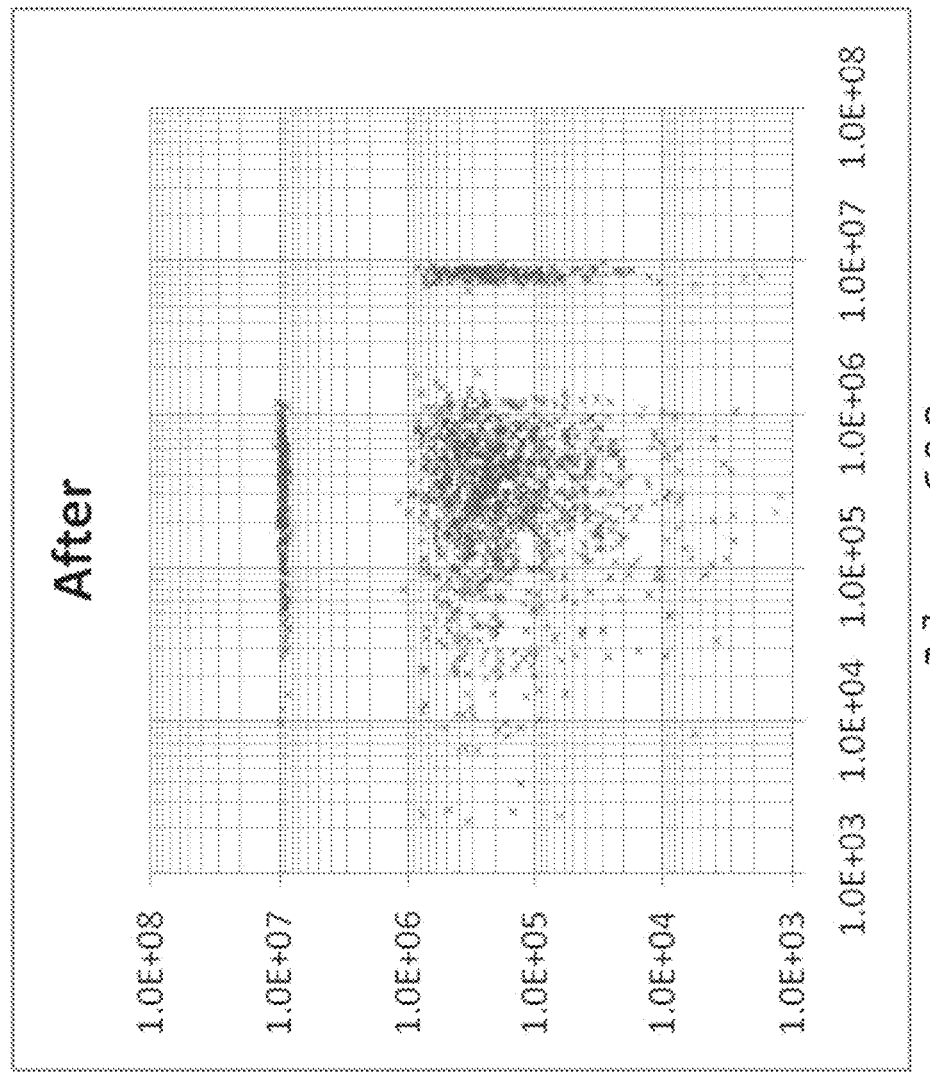

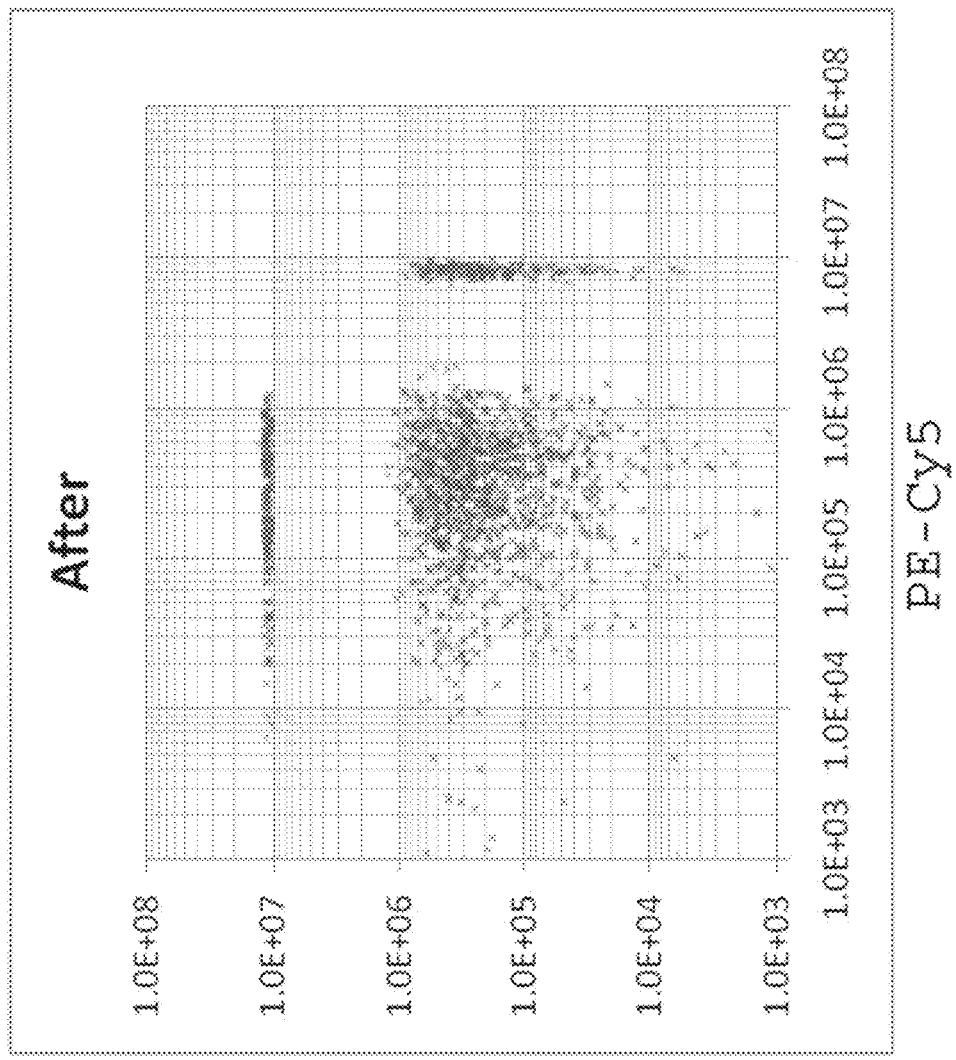

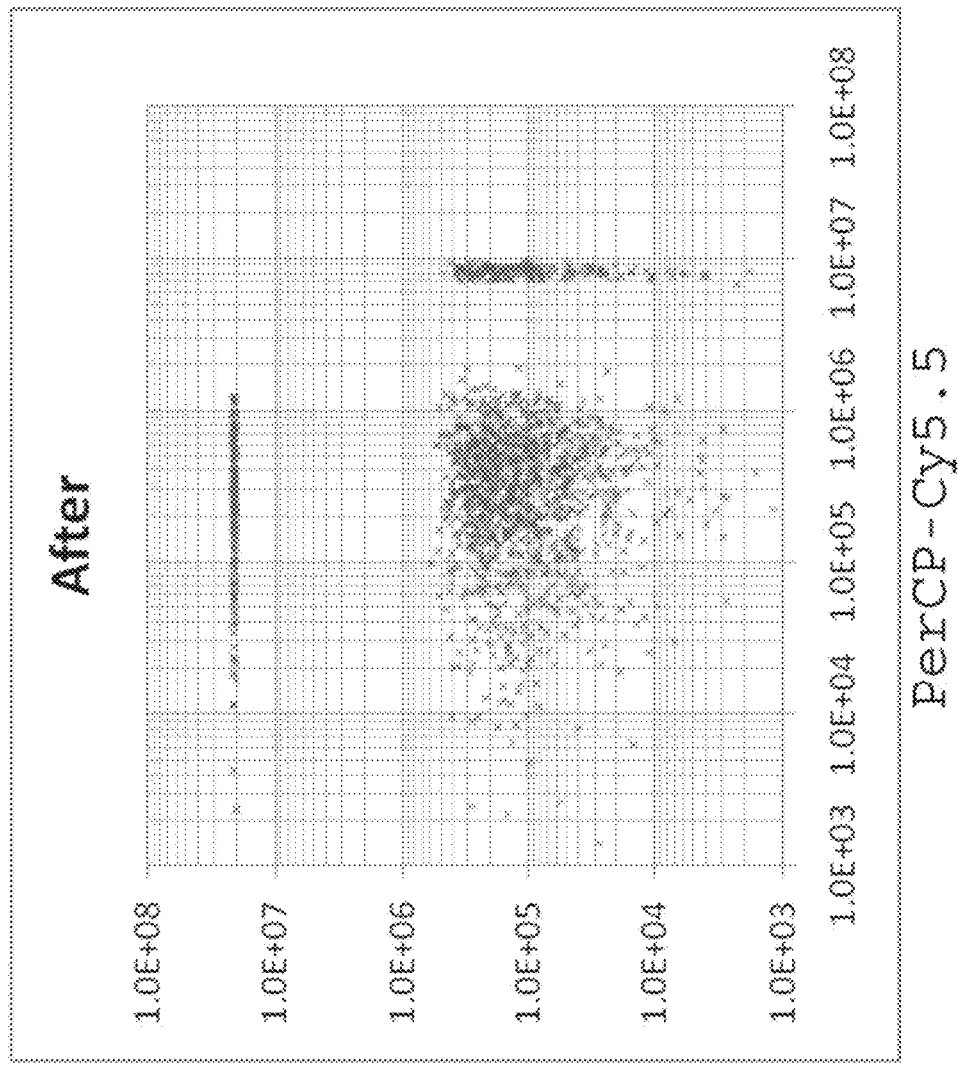

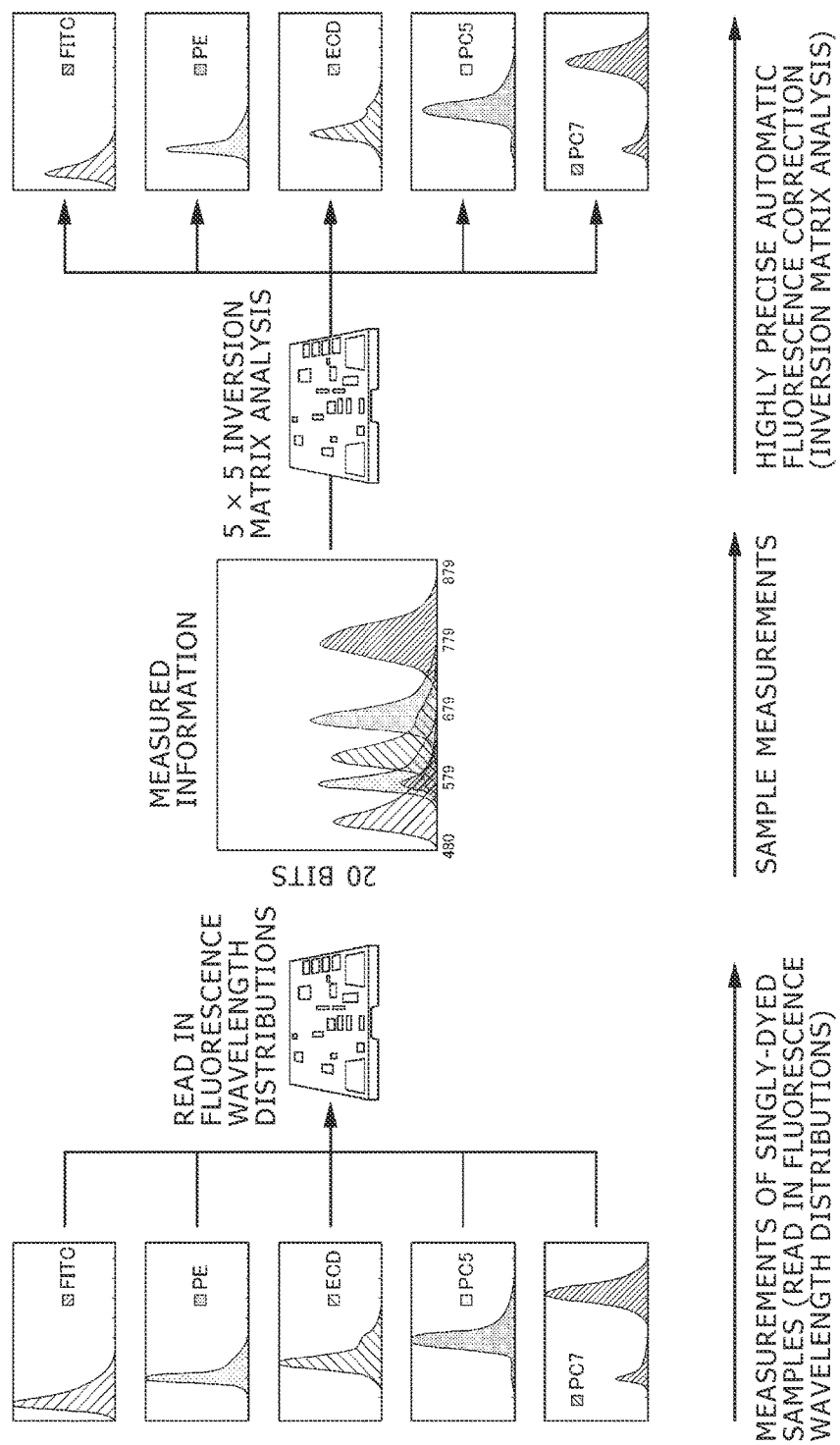

FIG.11

$$\begin{Bmatrix} FL1 \\ FL2 \\ FL3 \\ FL4 \\ FL5 \end{Bmatrix} = \begin{Bmatrix} a_{11} & a_{21} & a_{31} & a_{41} & a_{51} \\ a_{12} & a_{22} & a_{32} & a_{42} & a_{52} \\ a_{13} & a_{23} & a_{33} & a_{43} & a_{53} \\ a_{14} & a_{24} & a_{34} & a_{44} & a_{54} \\ a_{15} & a_{25} & a_{35} & a_{45} & a_{55} \end{Bmatrix}^{-1} \begin{Bmatrix} PMT1 \\ PMT2 \\ PMT3 \\ PMT4 \\ PMT5 \end{Bmatrix}$$

FL1~FL5 : TRUE FLUORESCENCE INTENSITIES OF FLUORESCENT DYES
an1~an5 : RATES OF WAVELENGTH DISTRIBUTIONS OF FLUORESCENT DYES n
PMT1~PMT5 : MEASURED FLUORESCENCE INTENSITIES

FLUORESCENCE INTENSITY CORRECTING METHOD, FLUORESCENCE INTENSITY CALCULATING METHOD, AND FLUORESCENCE INTENSITY CALCULATING APPARATUS

CROSS REFERENCES TO RELATED APPLICATIONS

The present application is a continuation of U.S. application Ser. No. 13/089,961, filed Apr. 19, 2011, which claims priority to Japanese Priority Patent Application JP 2010-104566 filed in the Japan Patent Office on Apr. 28, 2010, the entire content of which is hereby incorporated by reference.

BACKGROUND

The present application relates to a fluorescence intensity correcting method, a fluorescence intensity calculating method, and a fluorescence intensity calculating apparatus. More specifically, the application relates to a fluorescence intensity correcting method, a fluorescence intensity calculating method, and a fluorescence intensity calculating apparatus each of which is capable of precisely calculating intensities of fluorescences generated from plural fluorescent dyes, respectively, with which a microparticle is multiply-labeled.

Heretofore, there has been used an apparatus (such as a flow cytometer) for labeling a microparticle such as a cell with a fluorescent dye, and measuring an intensity or a pattern of a fluorescence generated from the fluorescent dye excited by radiating a laser beam to the microparticle, thereby measuring characteristics of the microparticle. In recent years, a multicolor measurement has been carried out in order to more minutely analyze the characteristics of the cell or the like. In this case, the multicolor measurement is such that a microparticle is labeled with plural fluorescent dyes, and lights generated from the respective fluorescent dyes are measured by using plural photodetectors (such as PMTs) corresponding to different received light wavelength bands, respectively. In the multicolor measurement, the fluorescent dyes agreeing in fluorescence wavelength with the received light wavelength bands of the respective photodetectors are selected and used.

On the other hand, fluorescence central wavelengths of the fluorescent dyes (such as FITC, phycoerythrin (PE) and allophycocyanin (APC)) are close to one another. Thus, the wavelength band exists in which the fluorescence spectra overlap one another. Therefore, in the case where the multicolor measurement is carried out based on a combination of these fluorescent dyes, even when the fluorescences generated from the respective fluorescent dyes are separated from one another by the wavelength band by using an optical filter, the fluorescence generated from the fluorescent dye other than objective fluorescent dyes is leaked to the photodetectors in some cases. When the leakage of the fluorescence occurs, the fluorescence intensities measured by the respective photodetectors become larger than the true intensities of the fluorescences generated from the objective fluorescent dyes, and thus mismatch occurs in data.

Fluorescence correction (compensation) for subtracting the fluorescence intensity for the leakage from the fluorescence intensity measured by the photodetector is carried out in order to correct the mismatch in the data. The fluorescence correction is such that an electrical or mathematical correction is added to a pulse on a dedicated circuit so that the fluorescence intensity measured by the photodetector becomes the true intensity of the fluorescence generated from the objective fluorescent dye.

A method of expressing the fluorescence intensities measured by the respective photodetectors in the form of a vector, and causing an inversion matrix of a leakage matrix previously set to act on the vector, thereby calculating a true intensity of a fluorescence generated from an objective fluorescent dye is known as a method of mathematically carrying out the fluorescence correction. This method is described in Japanese Patent Laid-Open No. 2003-83894 (refer to FIGS. 10 and 11). The leakage matrix is created by analyzing the fluorescence wavelength distribution of the microparticle single-labeled with fluorescent dye, and the fluorescence wavelength distribution of the fluorescent dyes is arranged in the form of a column vector. In addition, an inversion matrix of the leakage matrix is referred to as "a correction matrix" as well.

SUMMARY

Since with the fluorescence intensity correcting method using the correction matrix, the inversion matrix of the leakage matrix is caused to act on the vector having the fluorescence intensities measured by the respective photodetectors as elements thereof, it is necessary that the leakage matrix is a square matrix.

A matrix size of the leakage matrix depends on the number of fluorescent dyes used and the number of photodetectors used. Therefore, in order that the correction matrix may be the square matrix, it is necessary that the number of fluorescent dyes used and the number of photodetectors used are equal to each other. FIGS. 10A to 10C and 11 exemplify the case where five color measurements are carried out by using five kinds of fluorescent dyes (FITC, PE, ECD, PC5, and PC7), and five photodetectors.

Recently, for the purpose of meeting user's need that the number of usable fluorescent dyes is desired to be increased in order to minutely analyze the characteristics of the cell or the like, an apparatus in which the number of photodetectors is increased has also been developed. In such an apparatus that a large number of photodetectors is disposed, the number of photodetectors used in the measurement may be larger than the number of fluorescent dyes used in the labeling for the microparticle in some cases. In such cases, for the purpose of effectively apply the fluorescence correction using the correction matrix, it is necessary that the number of fluorescent dyes used and the number of photodetectors used are equal to each other. Therefore, the measured data is utilized by suitably selecting the photodetectors whose number agrees with the number of fluorescent dyes without using the measured data obtained from all the photodetectors. For this reason, there is caused a problem that the resulting measured data is not effectively utilized.

The present application has been made in order to solve the problems described above, and it is therefore desirable to provide a fluorescence intensity correcting method, a fluorescence intensity calculating method, and a fluorescence intensity calculating apparatus each of which is capable of effectively utilizing measured data obtained from all photodetectors without depending on the number of fluorescent dyes in the case where a microparticle labeled with plural fluorescent dyes is multicolor-measured by plural photodetectors, thereby precisely calculating intensities of fluorescences generated from respective fluorescent dyes.

In order to attain the desire described above, according to an embodiment, there is provided a fluorescence intensity correcting method including the steps of: receiving fluorescences generated from plural fluorescent dyes excited by radiating a light to a microparticle multiply-labeled with the plural fluorescent dyes having fluorescence wavelength bands overlapping one another by photodetectors which correspond to different received light wavelength bands, respectively, and whose number is larger than the number of fluorescent dyes; and approximating measured spectra obtained by collecting detected values from the plural photodetectors based on a linear sum of single-dyeing spectra obtained from a microparticle individually labeled with the fluorescent dyes.

In the fluorescence intensity correcting method described above, the approximation of the measured spectra based on the linear sum of the single-dyeing spectra can be carried out by using a least-squares method. In addition, at this time, when an invalid value(s) is(are) contained in the detected values, the invalid detected value(s) may be excluded, and thus measured spectra may be approximated based on the linear sum of the single-dyeing spectra. By excluding the invalid detected value(s), a correction precision of the fluorescence intensity is enhanced.

Specifically, in the fluorescence intensity correcting method described above, a parameter ak (k=1 to m) at which an evaluation function expressed by following Expression gets a minimum value is obtained by using a normal equation or singular value decomposition, thereby making it possible to calculate intensities of the fluorescences generated from the fluorescent dyes, respectively:

$$\chi^2 = \sum_{i=1}^{N} \left[ \frac{y_i - \sum_{k=1}^{M} a_k X_k(x_i)}{\sigma_i} \right]^2$$

where $X_k(x_i)$ represents a detected value from the i-th photodetector in the single-dyeing spectrum of the k-th fluorescent dye, $y_i$ represents a detected value from the i-th photodetector in the measured spectra, and $\sigma_i$ represents a reciprocal number of a weight for the measured value from the i-th photodetector. In this case, the reciprocal number of the weight, for example, may be a measurement error variance of the i-th photodetector, or the like. If there is no reciprocal number of the weight, all $\sigma_i$ may be set as 1.

In addition, when the invalid value(s) is(are) contained in the detected values, in the fluorescence intensity correcting method described above, the parameter $a_k$ (k=1 to m) at which the evaluation function expressed by following Expressions gets the minimum value is obtained, thereby making it possible to calculate the intensities of the fluorescences generated from the respective fluorescent dyes:

$$\chi^2 = \sum_{i=1}^{N_1} \left[ \frac{y_i - \sum_{k=1}^{M} a_k X_k(x_i)}{\sigma_i} \right]^2$$

or $X'_k(x_i) = X_k(x_i) \ (k = 1 \sim M, i = 1 \sim N_1)$ $X'_k(x_i) = 0 \ (k = 1 \sim M, i = N_1 + 1 \sim N)$ $$\chi^2 = \sum_{i=1}^{N} \left[ \frac{y_i - \sum_{k=1}^{M} a_k X'_k(x_i)}{\sigma_i} \right]^2$$

where $X_k(x_i)$ represents a detected value from the i-th photodetector in the single-dyeing spectrum of the k-th fluorescent dye, $y_i$ represents a detected value from the i-th photodetector in the measured spectra, and $\sigma_i$ represents a reciprocal number of a weight for the measured value from the i-th photodetector. However, an invalid detected value is taken to be $y_i$ (i="$N_1$+1" to N), and a valid detected value is taken to be $y_i$ (i=1 to $N_1$).

According to another embodiment, there is provided a fluorescence intensity calculating method including the steps of: receiving fluorescences generated from plural fluorescent dyes excited by radiating a light to a microparticle multiply-labeled with the plural fluorescent dyes having fluorescence wavelength bands overlapping one another by photodetectors which correspond to different received light wavelength bands, respectively, and whose number is larger than the number of fluorescent dyes, and obtaining measured spectra by collecting detected values from the photodetectors; and approximating the measured spectra based on a linear sum of single-dyeing spectra obtained from the microparticle individually labeled with the fluorescent dyes, thereby calculating intensities of the fluorescences generated from the fluorescent dyes, respectively.

According to still another embodiment, there is provided a fluorescence intensity calculating apparatus including: a measuring section for receiving fluorescences generated from plural fluorescent dyes excited by radiating a light to a microparticle multiply-labeled with the plural fluorescent dyes having fluorescence wavelength bands overlapping one another by photodetectors which correspond to different received light wavelength bands, respectively, and whose number is larger than the number of fluorescent dyes, and obtaining measured spectra by collecting detected values from the photodetectors; and a calculating section for approximating the measured spectra based on a linear sum of single-dyeing spectra obtained from the microparticle individually labeled with the fluorescent dyes, thereby calculating intensities of the fluorescences generated from the fluorescent dyes, respectively.

In the present embodiment, biologically-relevant microparticles such as a cell, a microbe, and a liposome, synthetic particles such as a latex particle, a gel particle, and an industrial particle, and the like are generally contained in "the microparticles."

A chromosome, a liposome, a mitchondrion, an organelle (cell organelle), and the like composing various kinds of cells are contained in the biologically-relevant microparticles. An animal cell (such as a trilineage cell) and a plant cell are contained in the cells. A bacillo class such as a Bacillus coli, a virus class such as a tabacco mosaic virus, a fungus class such as a yeast fungus, and the like are contained in the microbes. In addition, a biologically-relevant polymer such as a nucleic acid, a protein, and a complex thereof may also be contained in the biologically-relevant microparticles. In addition, the industrial particle, for example, may also be an organic or inorganic polymer material, a metal or the like. Polystyrene, styrene, divinylbenzene, polymethyl methacrylate, or the like is contained in the organic polymer material. A glass, silica, a magnetic material or the like is contained in the inorganic polymer material. Also, gold colloid, aluminum or the like is contained in the metal. Although it is not out of the way that a shape of each of those microparticles is generally a spherical shape, the shape thereof may also be nonspherical shape, and a size, a mass and the like thereof are especially by no means limited.

In addition, in the present embodiment, "the invalid detected value" means a detected value having the obviously low reliability, and also a detected value having the possibility that when the detected value is used in the calculation, the precision of calculating the fluorescence intensity is reduced. For example, the detected value obtained in the photodetector corresponding to the wavelength out of the fluorescence wavelength band of a certain fluorescent dye as the received light wavelength band when the measurement about the microparticle single-labeled with the certain fluorescent dye is carried out, the detected value obtained in the photodetector when the measurement is carried out by radiating the light having the wavelength band out of the excited wavelength band to the microparticle single-labeled with a certain fluorescent dye, and the like are contained in the invalid detected value. These detected values ought not to be detected in theory. However, in the actual apparatus, from the reason that the fluorescence which should be mechanically shielded is leaked, the electrical noise is applied and so forth, these detected values are obtained in some cases. In addition, the characteristics of the specific photodetector become worse from some sort of reason, and as a result, such low reliable detected values are obtained in some cases.

As set forth hereinabove, according to the present embodiment, it is possible to provide the fluorescence intensity correcting method, the fluorescence intensity calculating method, and the fluorescence intensity calculating apparatus each of which is capable of effectively utilizing the measured data obtained from all the photodetectors without depending on the number of fluorescent dyes in the case where the microparticle labeled with the plural fluorescent dyes is multicolor-measured by the plural photodetectors, thereby precisely calculating the intensities of the fluorescences generated from the respective fluorescent dyes.

Additional features and advantages are described herein, and will be apparent from the following Detailed Description and the figures.

BRIEF DESCRIPTION OF THE FIGURES

FIG. 1 is a graphical representation explaining an approximated curves obtained by approximating measured spectra based on a linear sum of single-dyeing spectra;

FIG. 2 is a diagram explaining elements of a matrix of (N×M);

FIGS. 3A to 3D are a plot diagram before fluorescence correction in PE-PE-TR two-dimensional plotting in positive process control, a plot diagram obtained by executing fluorescence correction processing by using an inversion matrix method as an existing technique in the PE-PE-TR two-dimensional plotting in positive process control, a plot diagram obtained by executing fluorescence correction processing by using a least-squares method (normal equation) in the PE-PE-TR two-dimensional plotting in positive process control, and a plot diagram obtained by executing fluorescence correction processing by executing a least-squares method (SVD method) in the PE-PE-TR two-dimensional plotting in positive process control, respectively;

FIGS. 5A to 5K are plot diagrams each obtained by subjecting simulation data to the fluorescence correction processing by using the inversion matrix method as the existing method, respectively;

FIGS. 6A to 6K are plot diagrams each obtained by subjecting simulation data to fluorescence correction processing by using a least-squares method in the present embodiment, respectively;

FIGS. 10A to 10C are diagrams explaining a fluorescence correcting method using an existing correction matrix; and FIG. 11 is a diagram explaining matrix elements of the existing correction matrix.

DETAILED DESCRIPTION

Figure 3B:
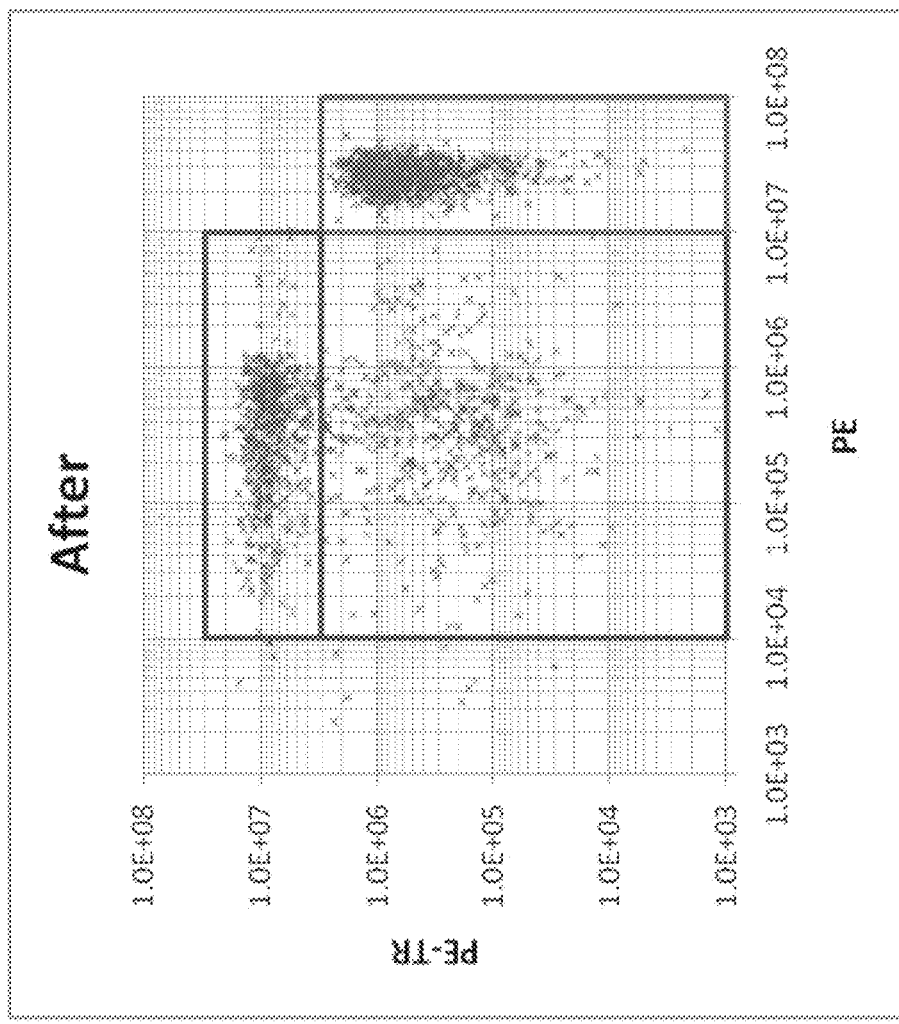

Embodiments of the present application will be described below in detail with reference to the drawings.

The preferred embodiments of the present application will be described in detail hereinafter with reference to the accompanying drawings. It is noted that embodiments of the present application which will be described below merely examplifies typical embodiments of the present application, and thus the scope of the present application is not intended to be construed in a limiting sense by the embodiments. It is also noted that the description will be given below in accordance with the following order.

1. Fluorescence Intensity Correcting Method
(1-1) Approximated Curves
(1-2) Linear Least-Squares Equation
(1-2-1) Normal Equation
(1-2-2) Singular Value Decomposition
2. Fluorescence Intensity Calculating Method
(2-1) Labeling
(2-2) Measurement
(2-3) Fluorescence Intensity Calculation
3. Fluorescence Intensity Calculating Apparatus
1. Fluorescence Intensity Correcting Method
(1-1) Approximated Curves The feature of the fluorescence intensity correcting method according to a first embodiment is that measured spectra are approximated based on a linear sum of single-dyeing spectra, thereby calculating true intensities of fluorescences generated from respective fluorescent dyes. "The measured spectra" are obtained by receiving fluorescences generated from fluorescent dyes excited by radiating a light to a microparticle multiply-labeled with plural fluorescent dyes having fluorescence wavelength bands overlapping one another by photodetectors which correspond to different received light wavelength bands and which number is larger than the number of fluorescent dyes, and collecting detected values from the respective photodetectors. In addition, "the single-dyeing spectra" are fluorescence wavelength distributions of the respective fluorescent dyes, and are obtained by receiving fluorescences generated from fluorescent dyes excited by radiating a light to a microparticle individually labeled with fluorescent dyes by photodetectors, respectively, and by collecting detected values from the respective photodetectors.

An approximated curve which is obtained by approximating measured spectra based on a linear sum of single-dyeing spectra will now be described with reference to FIG. 1.

In FIG. 1, an X-axis represents an observation point, and a Y-axis represents a detected value. In FIG. 1, a detected value of a fluorescence received by a photodetector $x_1$ is indicated by $y_1$, a detected value of a fluorescence received by a photodetector $x_2$ is indicated by $y_2$, and a detected value of a fluorescence received by a photodetector $x_n$ is indicated by $y_n$. A line connecting the detected values $y_1$ to $y_n$ is a measured spectrum.

In addition, in FIG. 1, a curve (basis function) representing a single-dyeing spectrum of a first fluorescent dye (fluorescent dye 1) is indicated by $X_1(x)$, a curve representing a single-dyeing spectrum of a second fluorescent dye (fluorescent dye 2) is indicated by $X_2(x)$, and a curve representing a single dyeing spectrum of an m-th fluorescent dye (fluorescent dye m) is indicated by $X_m(x)$.

With the photodetectors, the fluorescences from all the fluorescent dyes of the fluorescent dye 1 to the fluorescent dye m are received in a state in which those fluorescences are leaked at predetermined rates, respectively. For this reason, the detected values obtained from the respective photodetectors can be approximated as a sum of values obtained by multiplying basis functions of the fluorescent dye 1 to the fluorescent dye m by the respective predetermined rates in accordance with Expression (4):

$$y(x) = \sum_{k=1}^{M} a_k \cdot X_k(x) \tag{4}$$

where $a_k$ represents the rate of the leakage of the fluorescence from the fluorescent dye k to the photodetector $x_k$. Here, the rate $a_k$ of the leakage of the fluorescence from the fluorescent dye k to the photodetector $x_k$ is regulated by the fluorescence intensity (true fluorescence intensity) of the fluorescent dye k.

Specifically, for example, the detected value $y_1$ obtained from the photodetector $x_1$ is approximated as a sum $y(x_1)$ of a value obtained by multiplying the basis function $X_1(x_1)$ of the fluorescent dye 1 by the rate $a_1$ to a value obtained by multiplying the basis function $X_m(x_1)$ of the fluorescent dye m by the rate $a_m$. Also, the leakage rates $a_k$ (k=1 to m) of the fluorescences of the fluorescent dyes 1 to m to the photodetector $x_1$ correspond to the fluorescence intensities of the fluorescent dyes 1 to m, respectively.

An approximated curve represented by Expression (4) is obtained by obtaining the leakage rate $a_k$ by using a linear least-squares method which will next be described. The leakage rate $a_k$ is equal to the true fluorescence intensity of the corresponding one of the fluorescent dyes.

(1-2) Linear Least-Squares Method

For obtaining $a_k$, firstly, an evaluation function (chi-square) expressed by Expression (5) is defined. Also, such a parameter $a_k$ (k=1 to m) at which Expression (5) gets a minimum value is obtained.

$$\chi^2 = \sum_{i=1}^{N} \left[ \frac{y_i - \sum_{k=1}^{M} a_k X_k(x_i)}{\sigma_i} \right]^2 \tag{5}$$

where $\sigma_i$ represents a reciprocal number of a weight for the measured value from the i-th photodetector. In this case, the reciprocal number of the weight, for example, may be a measurement error variance of the i-th photodetector. If there is no reciprocal number of the weight, all $\sigma_i$ may be set as 1.

(1-2-1) Normal Equation

Next, a matrix A of (N×M) (refer to FIG. 2) composed of elements expressed by Expression (6), and a vector b having a length N (Expression (7)) are both defined, and a vector in which M parameters $a_1$ to $a_m$ obtained from application is set as a.

$$A_{ij} = \frac{X_j(x_i)}{\sigma_i} \tag{6}$$

$$b_i = \frac{y_i}{\sigma_i} \tag{7}$$

Expression (5) gets a minimum value when all values obtained by differentiating $\chi^2$ by M parameters $a_k$ become zero.

$$0 = \sum_{i=1}^{N} \frac{1}{\sigma_i^2} \left[ y_i - \sum_{j=1}^{M} a_j X_j(x_i) \right] \cdot X_k(x_i) \tag{8}$$

$$k = 1, \ldots, M$$

When the order for obtaining the sum is changed, Expression (8) can be transformed into Expression (9) as a matrix equation (normal equation):

$$\sum_{j=1}^{M} a_{kj} a_j = \beta_k \tag{9}$$

where $[a_{kj}]$ represents a matrix of (M×N), and $[\beta_k]$ represents a vector having a length M.

$$a_{kj} = \sum_{i=1}^{N} \frac{X_j(x_i) \cdot X_k(x_i)}{\sigma_j^2}$$

that is, $$[\alpha] = A^T \cdot A \tag{10}$$

$$\beta_k = \sum_{i=1}^{N} \frac{y_i \cdot X_k(x_i)}{\sigma_i^2}$$

that is, $$[\beta] = A^T \cdot b \tag{11}$$

Therefore, when Expression (8) described above is expressed in the form of a matrix, Expression (12) is obtained as follows.

$$[\alpha] \cdot a = [\beta] \text{ or } (A^T \cdot A) \cdot a = A^T \cdot b \tag{12}$$

Expression (12) is a simultaneous linear equation with M unknowns, and thus $a_j$ is obtained by solving Expression (12).

(1-2-2) Singular Value Decomposition

Instead of utilizing the method using the normal equation described above, a vector in which $a_1$ to $a_m$ as M parameters may also be obtained by utilizing singular value decomposition.

The singular value decomposition (SVD) is based on the theorem of a linear algebra in which an arbitrary matrix A of (N×M) is written in the form of the product of three matrices of U, W and $V^T$ (refer to Expression (13)). The matrix U is a column orthogonal matrix of (N×M), the matrix W is a diagonal matrix of (M×M) (a diagonal component $w_i$ is non-negative and is a referred to as a singular value), the matrix $V^T$ is a transposition of an orthogonal matrix V of (M×M). In addition, the matrices U and V are the orthonormal matrices. In this case, the columns are orthonormal to one another (refer to Expression (14)).

$$(A) = UWV^T = (U) \cdot \begin{pmatrix} w_i & & & \\ & w_2 & & \\ & & \ddots & \\ & & & \ddots \\ & & & & w_N \end{pmatrix} \cdot (V^T) \quad (13)$$

$$(U^T) \cdot (U) = (V^T) \cdot (V) = (1) \quad (14)$$

Expression (5) described above can be rewritten as Expression (15):

$$\chi^2 = |A \cdot a - b|^2 \quad (15)$$

When the matrix A is subjected to the singular value decomposition to obtain the matrices U, W and V as with Expression (13) described above, the vector, a, which minimizes Expression (15) is obtained from Expression (16). This operation is called backward substitution. If there is a sufficiently small value in $w_i$, $1/w_i$ is replaced with 0 and the processing is advanced.

$$a = V \cdot [\text{diag}(1/w_i)] \cdot (U^T \cdot b) \quad (16)$$

2. Fluorescence Intensity Calculating Method

Next, a description will be given with respect to a fluorescence intensity calculating method according to a second embodiment to which the fluorescence intensity correcting method of the first embodiment described above is applied.

(2-1) Labeling

Firstly, the microparticle as an object of the measurement is labeled with plural fluorescent dyes. The labeling of the fluorescent dye is generally carried out by coupling a fluorescent-labeled antibody to a molecule(s) existing on a surface of a microparticle. Although the fluorescent dye is especially by no means limited, for example, there are given phycoerythlin (PE), FITC, PE-Cy5, PE-Cy7, PE-Texas red, allophycocyanin (APC), APC-Cy7, ethidium bromide, propidium iodide, hoechst 33258/33342, DAPI, acridine orange, chromomycin, mithramycin, olivomycin, pyronin Y, thiazole orange, rhodamine 101 isothiocyanate, BCECF, BCECF-AM, C.SNARF-1, C.SNARF-1-AMA, aequorin, Indo-1, Indo-1-AM, Fluo-3, Fluo-3-AM, Fura-2, Fura-2-AM, oxonole, Texas red, rhodamine 123, 10-N-nonyl-acridine orange, fluorescein, fluorescein diacetate, carboxyfluorescein, caboxyfluorescein diacetate, carboxydichlorofluorescein, carboxydichlorofluorescein diacetate, and the like.

(2-2) Measurement

The microparticle labeled with the fluorescent dyes is measured by using a multicolor measuring apparatus in which photodetectors which correspond to different received light wavelength bands and whose number is larger than the number of fluorescent dyes are disposed. Also, the detected values obtained from the respective photodetectors are collected to obtain the measured spectra. The movement manipulation can be carried out similarly to the case of the method which is normally carried out.

(2-3) Fluorescence Intensity Calculation

The measured spectra are approximated based on the linear sum of the single-dyeing spectra in accordance with the method described above, thereby calculating the true fluorescence intensities generated from the respective fluorescent dyes. At this time, when the measurement error variance in the photodetector is not clear, all σi in Expression (5) may be set as 1. The single-dyeing spectra may be obtained by preparing the sample individually labeled with the fluorescent dyes whenever the measurement is carried out, or the standard spectra whose data is previously stored may be utilized.

3. Fluorescence Intensity Calculating Apparatus

The fluorescence intensity calculating apparatus according to a third embodiment is composed of a fluid system, an optical system, a sorting system, a data processing system, and the like similarly to the case of the existing flow cytometer or the like.

The fluid system is a section for causing a sample liquid containing therein microparticles as an object of a measurement to flow to a center of a laminar flow of a sheath liquid in a flow cell, thereby arranging the microparticles in a line within the flow cell. Instead of using the flow cell, the microparticles may be arranged in a line within a flow path formed on a microchip.

The optical system is a measuring section for receiving fluorescences generated from fluorescent dyes excited by radiating a light to a microparticle labeled with the fluorescent dyes by photodetectors, and collecting detected values from the respective photodetectors, thereby obtaining measured spectra. With the optical system, a scattered light such as a forward scattered light, a side scattered light, a Rayleigh scattered light, or a Mie scattered light is also detected. Specifically, the optical system is composed of a laser light source, a radiating system and a detecting system. In this case, the radiating system is composed of a condensing lens and a dichroic mirror for condensing and radiating a laser beam to the microparticle, a band-pass filter, and the like. Also, the detecting system detects the fluorescence and the scattered light generated from the microparticle by radiating the laser beam to the microparticle. The detecting system, for example, is composed of a photo multiplier tube (PMT), an area image pickup element such as a CCD or a CMOS element, and the like. Also, the photodetectors corresponding to different received light wavelength bands, respectively, are disposed in the detecting system.

When the microparticles are intended to be sorted, a sample liquid is ejected as droplets containing therein the respective microparticles to a space in the outside of the flow cell, and a movement directions of the droplets are controlled, thereby sorting the microparticle having desired characteristics. The sorting system is composed of a vibrating element such as a piezo element, a charging section, paired electrodes, and the like. In this case, the vibrating element changes the sample liquid into the droplets and discharges the droplets from the flow cell. The charging section charges the droplets ejected with the electric charges. Also, the paired electrodes are disposed to face each other along the movement directions of the droplets through the moving droplets.

The detected values are input as electrical signals from the photodetectors to the data processing system. The data processing system analyzes the optical characteristics of the microparticles based on the electrical signals. Also, the data processing system approximates the measured spectra obtained by collecting the detected values from the respective photodetectors based on the linear sum of the single-dyeing spectra in accordance with the method described above, thereby calculating the true fluorescence intensities generated from the respective fluorescent dyes. For this reason, the data processing system has a recording medium, such as a hard disc, for storing therein a program for executing the steps of the fluorescence intensity calculating method described above according to the second embodiment, a CPU for executing the program, a memory, and the like.

Example 1

Measured data obtained from the analysis using positive process control (whole blood control specimen) (Immuno-Trol, Beckman-Coulter, Inc.) for a commercially available flow cytometry was processed by the existing fluorescence correcting method using an inversion matrix, and the fluorescence correcting method according to the first embodiment. Also, the processing results were compared and examined.

The labeling for Immuno-Trol was carried out by using four kinds of fluorescence reagents of FITC, PE, PE-TR, and PE-Cy5 in accordance with an accompanying appended document. FIGS. 3A to 3D are PE-PE-TR two-dimensional plot diagrams obtained when the gate is applied to a cell group which seems likely to be lymphocytes in an FITC-SSC two-dimensional plot diagram, respectively.

FIG. 3A is a two-dimensional plot diagram when PMT (CH15) having a peak when the PE single-dyeing spectrum is measured is plotted on an axis of abscissa, and PMT (CH19) having a peak when the PE-TR single-dyeing spectrum is measured is plotted on an axis of ordinate. Also, FIG. 3A corresponds to a plot diagram before the fluorescence correction is carried out.

Figure 3D:
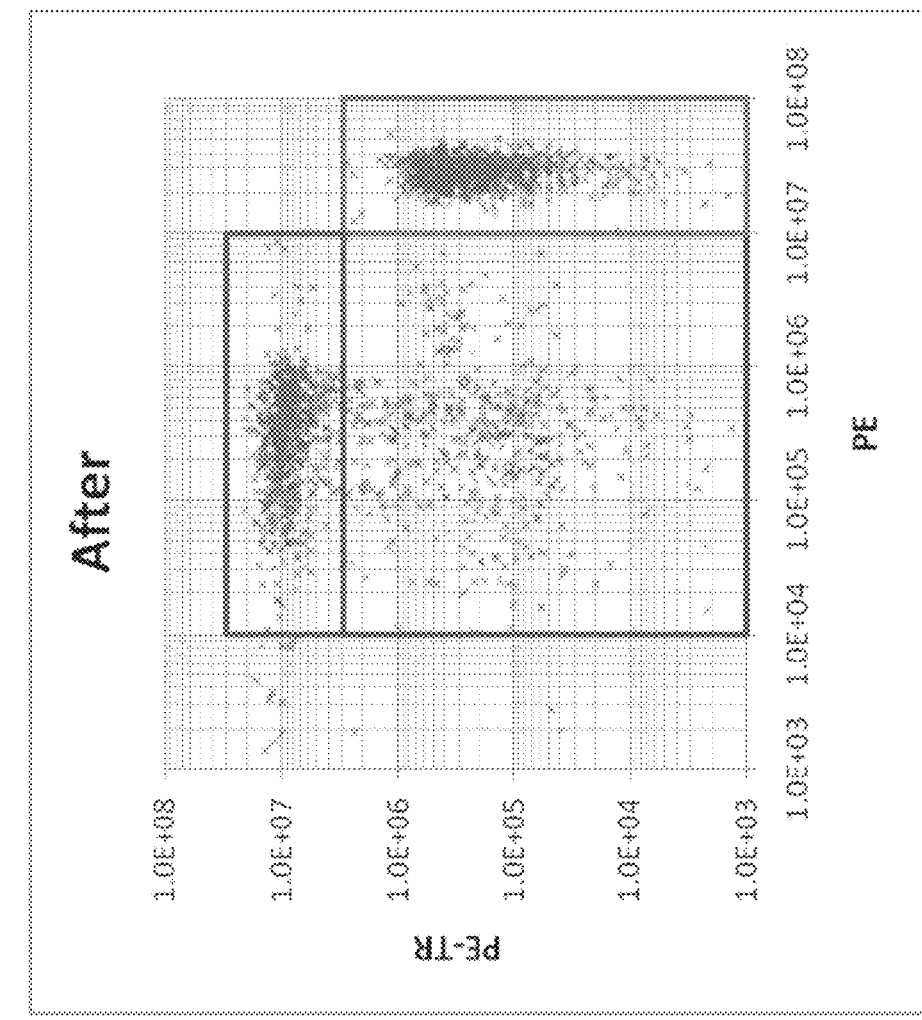

FIG. 3B is a plot diagram obtained by executing fluorescence correcting processing by using an inversion matrix method as the existing technique. FIG. 3C is a plot diagram obtained by executing the fluorescence correcting processing by using a least-squares method (normal equation). Also, FIG. 3D is a plot diagram obtained by executing the fluorescence correcting processing by using the least-squares method (SVD method).

Figure 4:
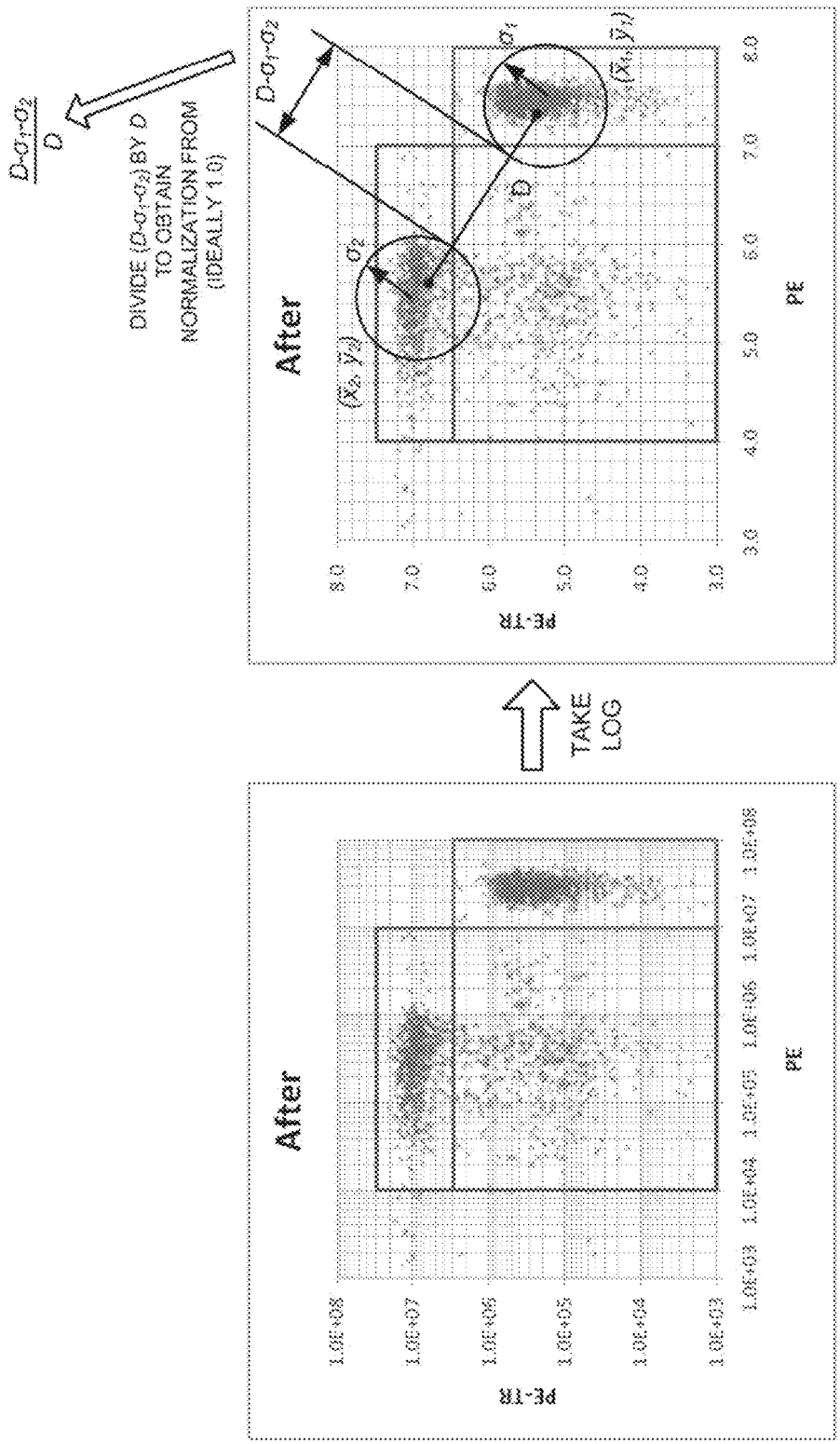
FIG. 4 is a diagram explaining definition of an index in accordance with which right and wrong of separation between cell groups are evaluated.
Figure 5A:
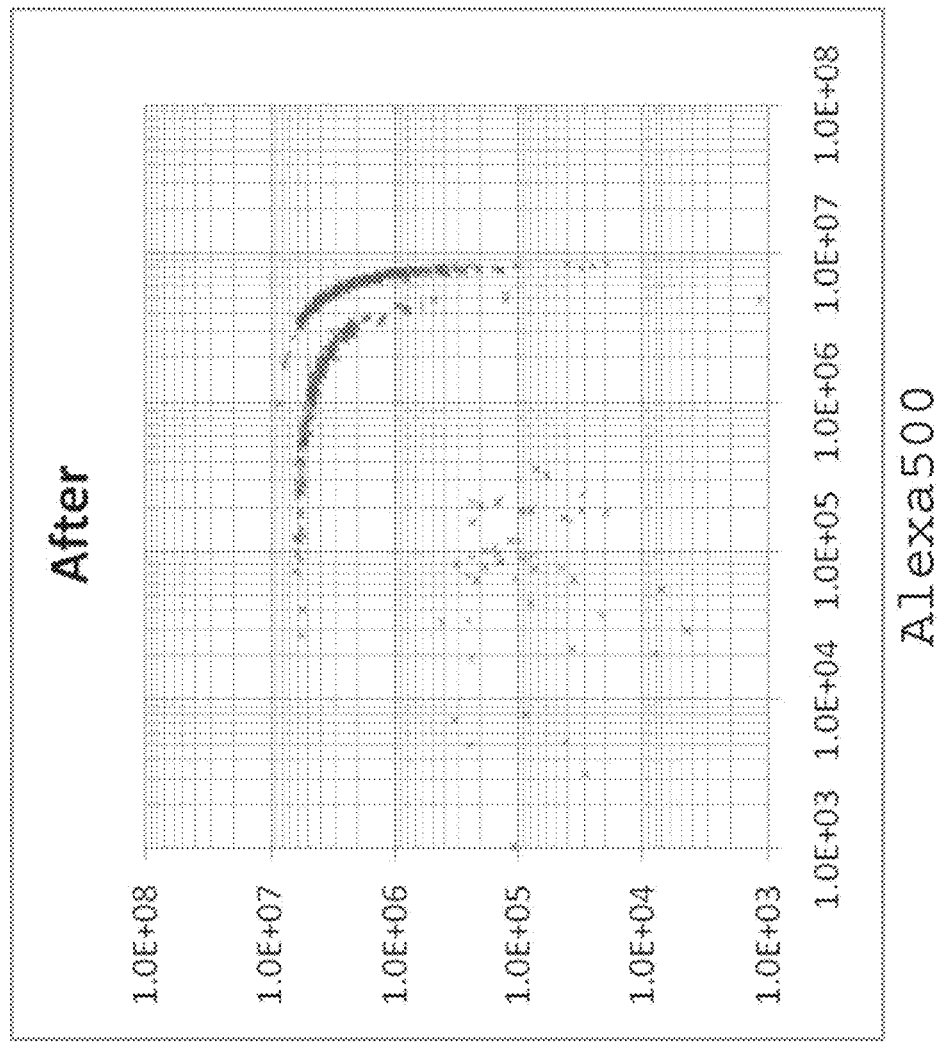
Figure 5B:
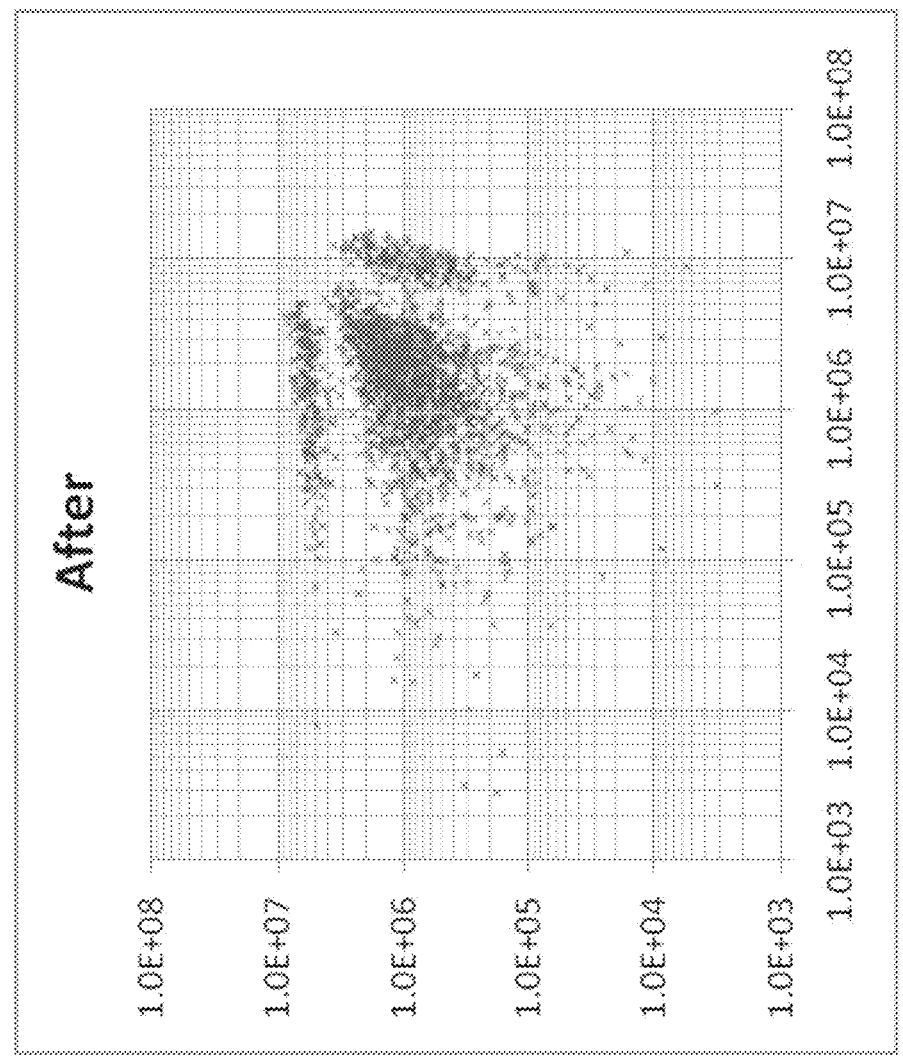
Figure 5E:
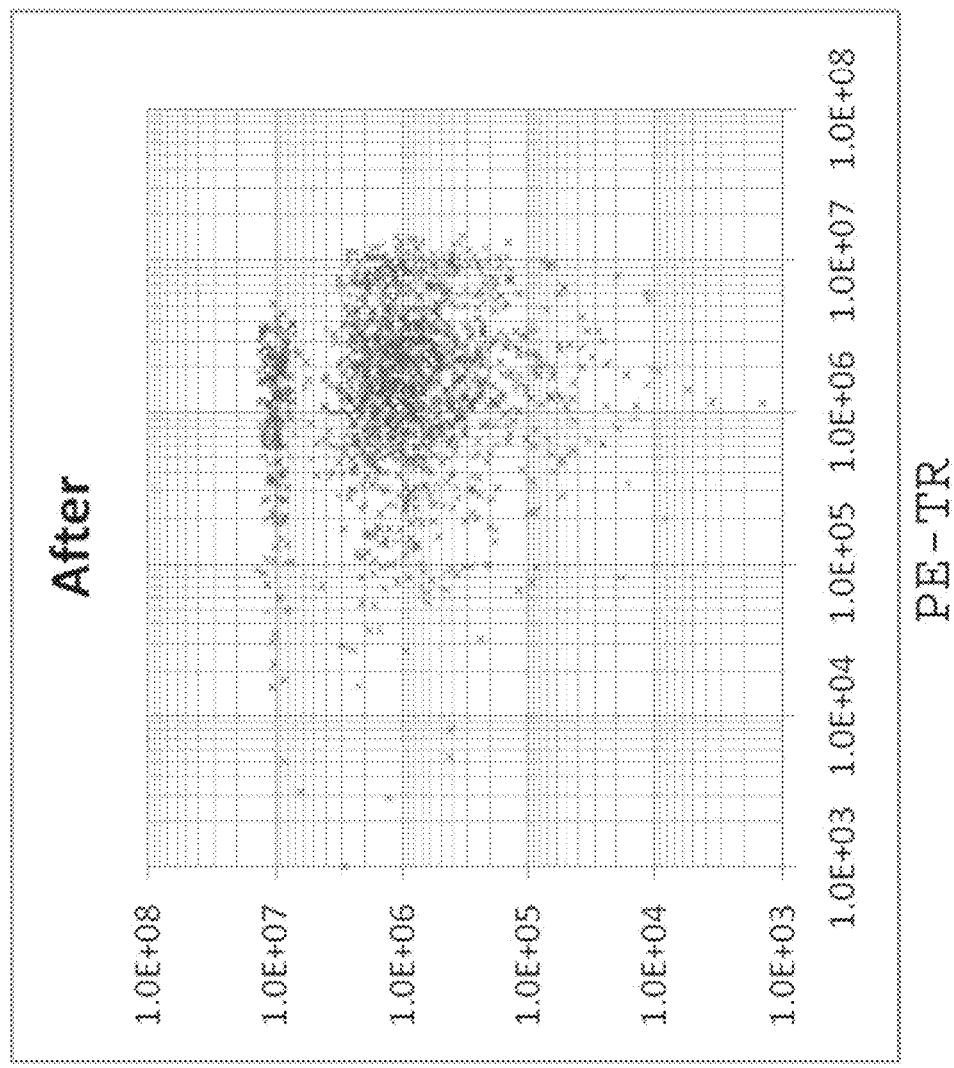
Figure 5G:
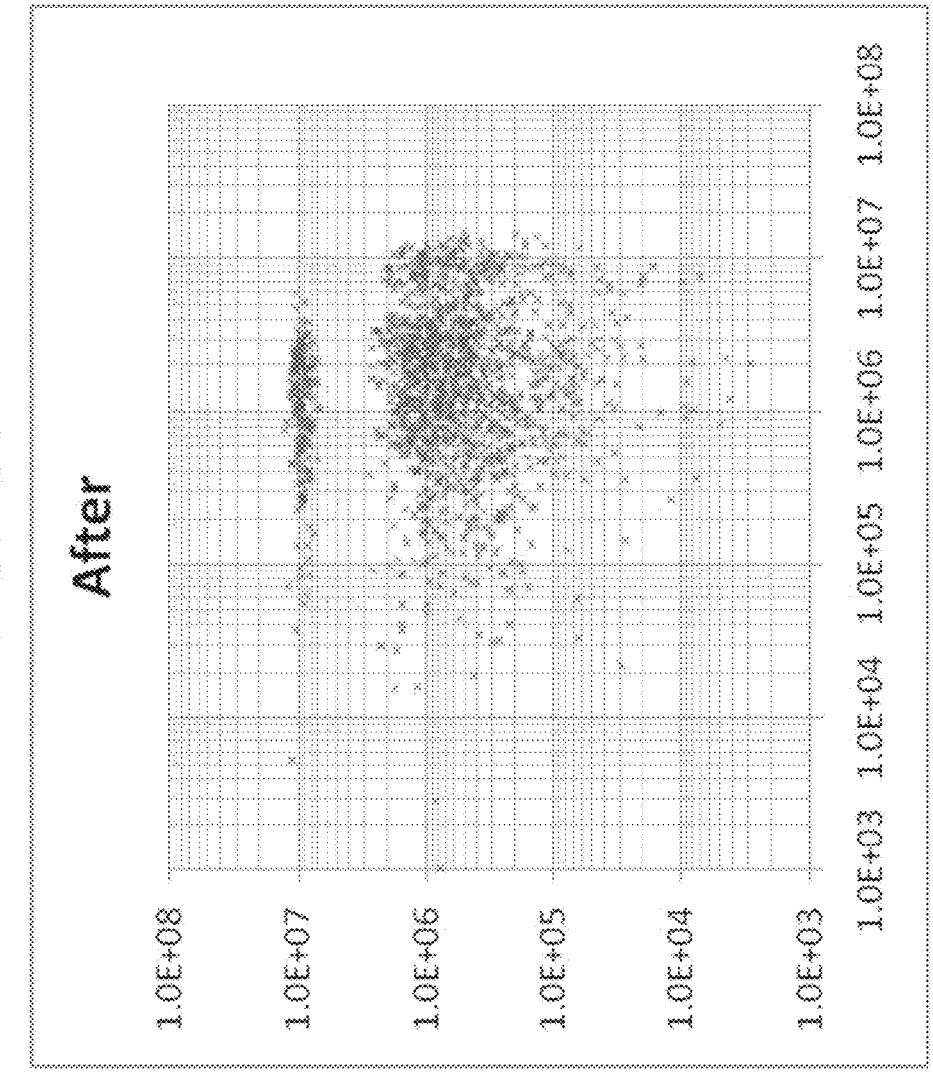
Figure 5I:
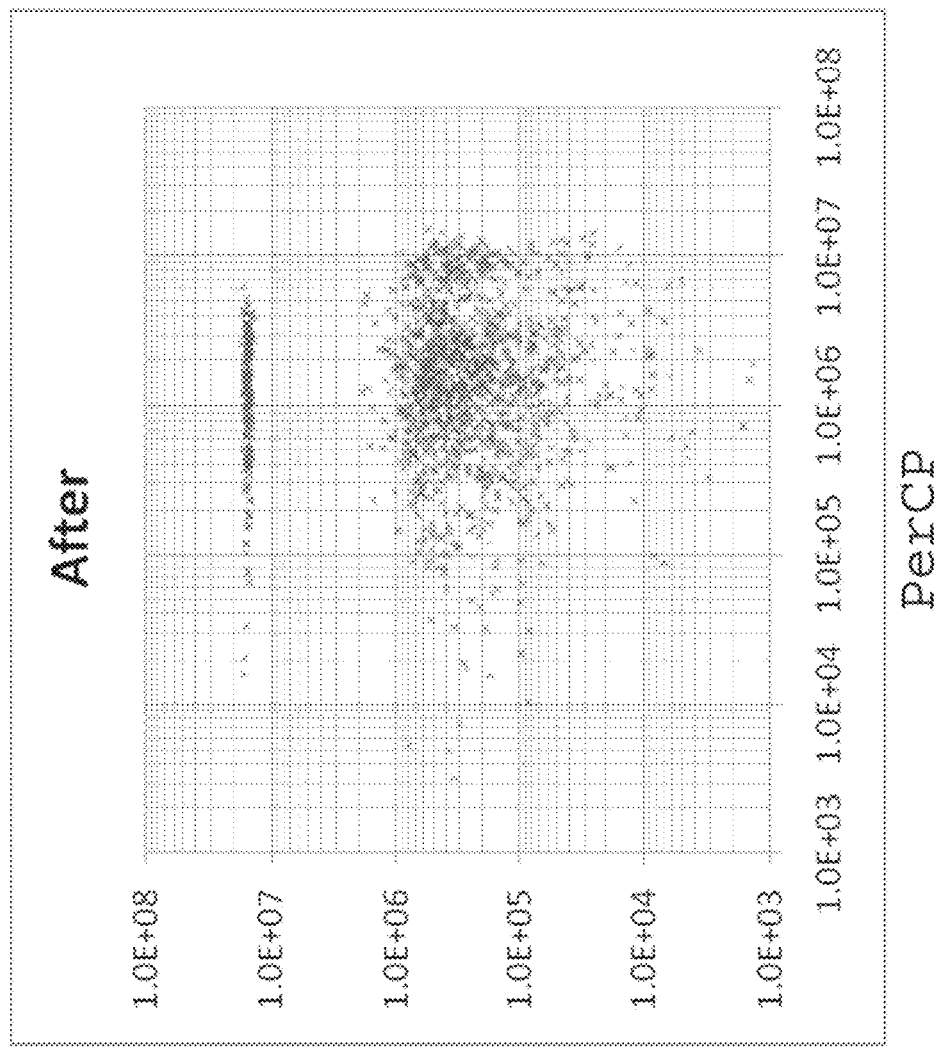
Figure 5J:
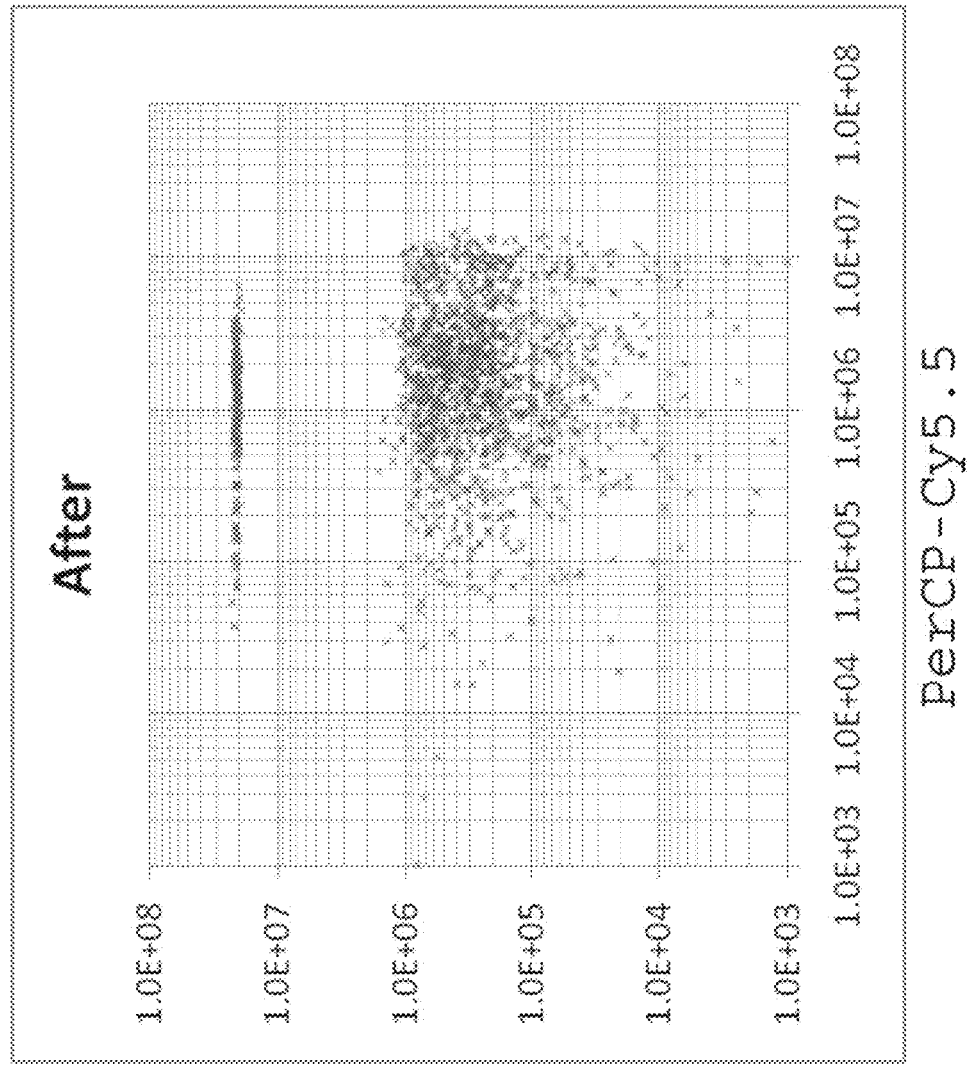
Figure 6B:
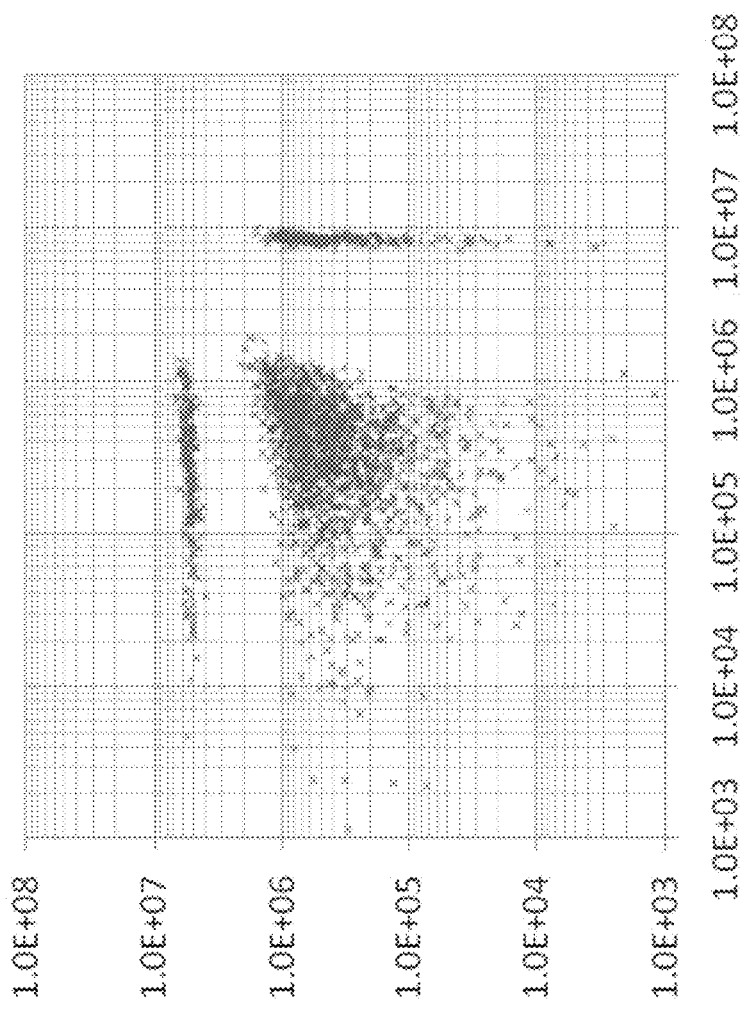
Figure 6F:
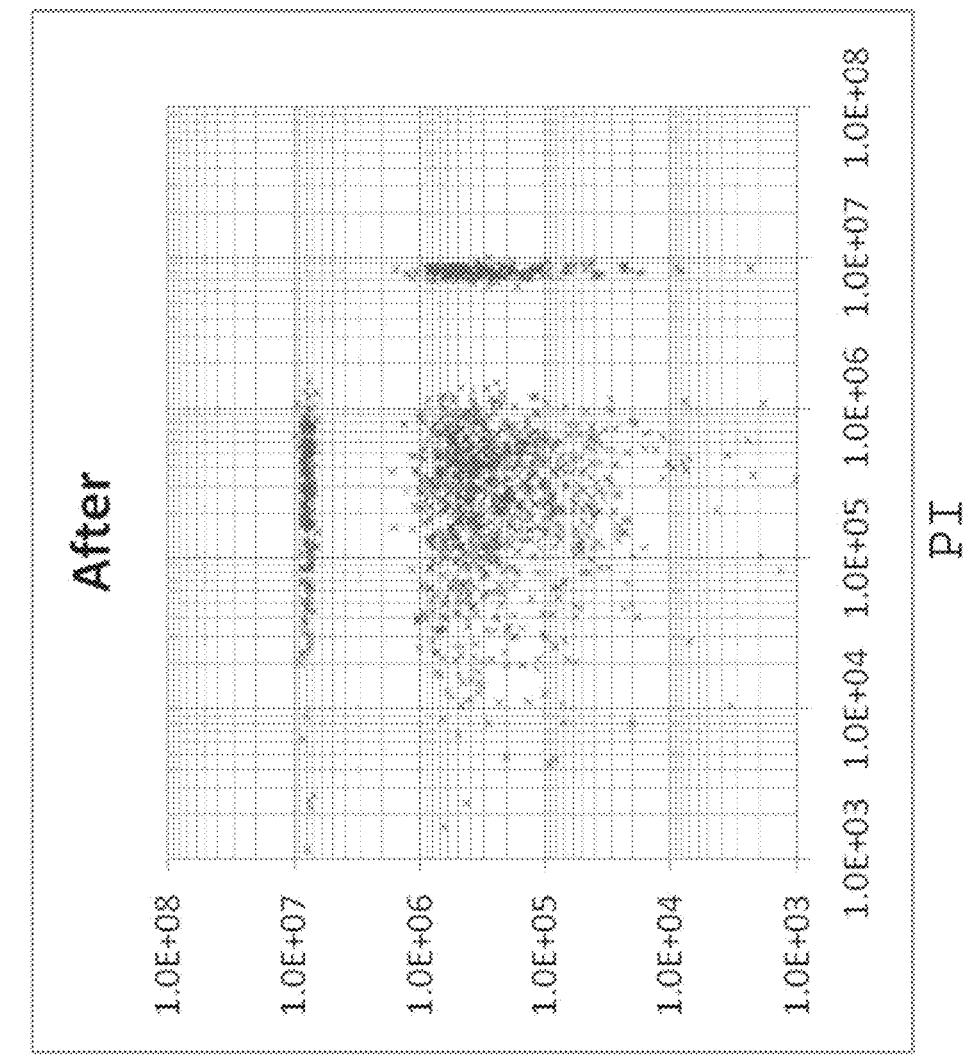
Figure 6I:
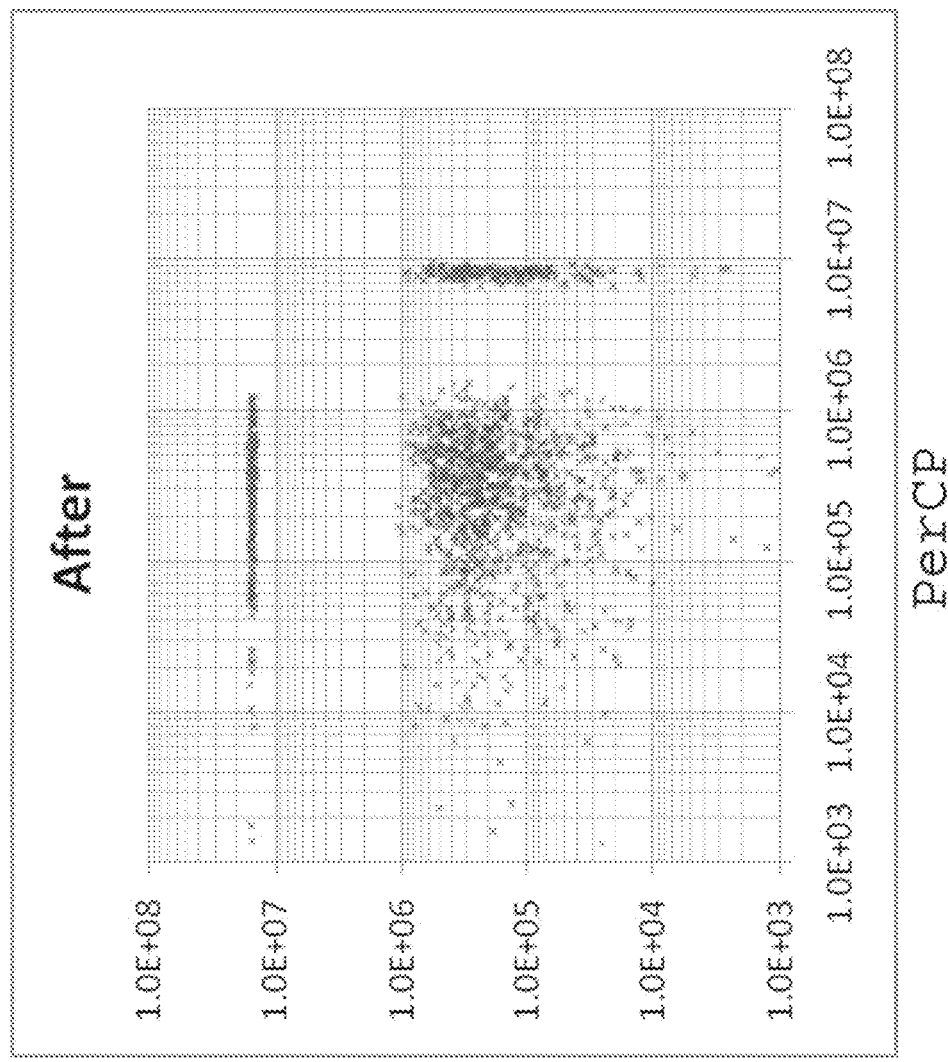
Figure 6K:
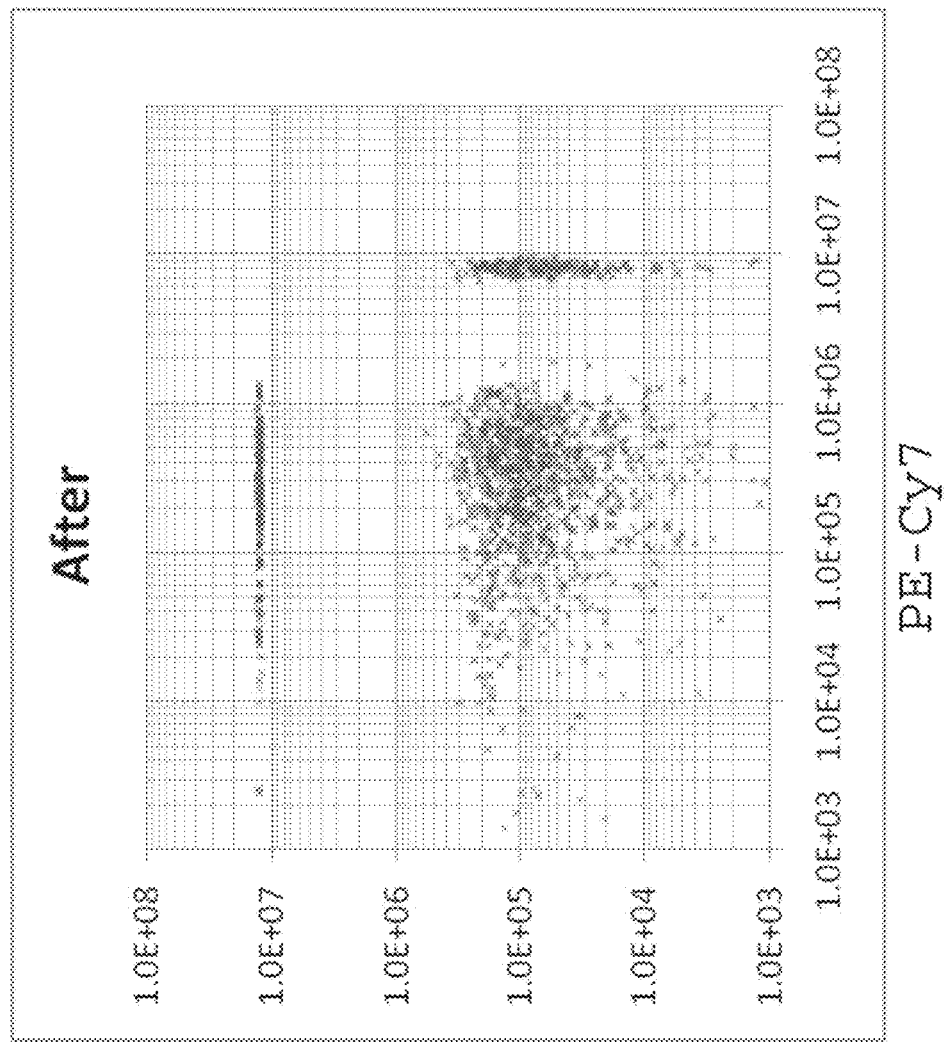

In each of the plot diagrams shown in FIGS. 3A to 3D, respectively, an index in accordance with which right and wrong of the separation between the cell groups were evaluated was defined as follows. That is to say, in each of the plot diagrams, Log (logarithms) was taken, and central coordinates and a standard deviation were obtained with respect to the PE positive cell group and the PE-TR positive cell group. Also, a mutual center-to-center distance was taken to be D, and the two standard deviations were taken to be σ1 and σ2, respectively (refer to FIG. 4). Also, a math formula of $(D-\sigma1-\sigma2)/D$" was made an index representing the separation between the cell groups. This index means that as a value of the index is larger, the separation between the cell groups is good and the performance of the fluorescence correcting processing is favorable.

The indices in the PE-TR-PE two-dimensional plot diagram, the PE-Cy5-PE two-dimensional plot diagram, and the PE-Cy5-PE-TR two-dimensional plot diagram shown in FIGS. 3A to 3D are summarized in "TABLE 1".

TABLE 1

| two-dimensional plot diagram (axis of ordinate/axis of abscissa) | inversion matrix method | least-squares method (normal equation · SVD method) |
|---|---|---|
| PE-TR/PE | 0.59 | 0.64 |
| PE-Cy5/PE | 0.61 | 0.65 |
| PE-Cy5/PE-TR | 0.31 | 0.76 |

In all the two-dimensional plot diagrams, the index has a larger value in the plot diagram obtained by executing the fluorescence correcting processing based on the least-squares method (the normal equation or the SVD method) than in the plot diagram obtained by executing the fluorescence correcting processing based on the inversion matrix method. As a result, it is possible to confirm that the fluorescence correcting method according to the first embodiment provides the favorable separation between the cell groups.

In addition, FIGS. 5A to 5K, and FIGS. 6A to 6K show two-dimensional plot diagrams, respectively, obtained by processing simulation data based on which a spectrum waveform containing therein a noise is generated at random on the assumption that twelve kinds of fluorescence reagents of FITC, Alexa 500, Alexa 514, Alexa 532, PE, PE-TR, PI, Alexa 600, PE-Cy5, PerCP, PerCP-Cy5.5, and PE-Cy7 are used. In FIGS. 5A to 5K, and FIGS. 6A to 6K, all FITCs are plotted on the axis of abscissa, and the fluorescent dye written on an upper side of each of the graphs is plotted on the axis of ordinate. In the case of the graph show in FIG. 4, the fluorescence correction is carried out by using the method utilizing the inversion matrix method as the existing method. Also, in the case of the graphs shown in FIGS. 5A to 5K, the fluorescence correction is carried out by using the method utilizing the least-squares method in the present embodiment. It is understood that although there are some plots which cannot be separated in the case of the inversion matrix method, all the plots can be satisfactorily separated in the case of the present embodiment.

Example 2

The measured data in which the invalid value(s) is(are) contained, and the measured data in which the invalid detected value(s) is(are) excluded were processed by using the fluorescence intensity correcting method utilizing the least-squares method. Also, the processing results were compared and examined.

Figure 7:
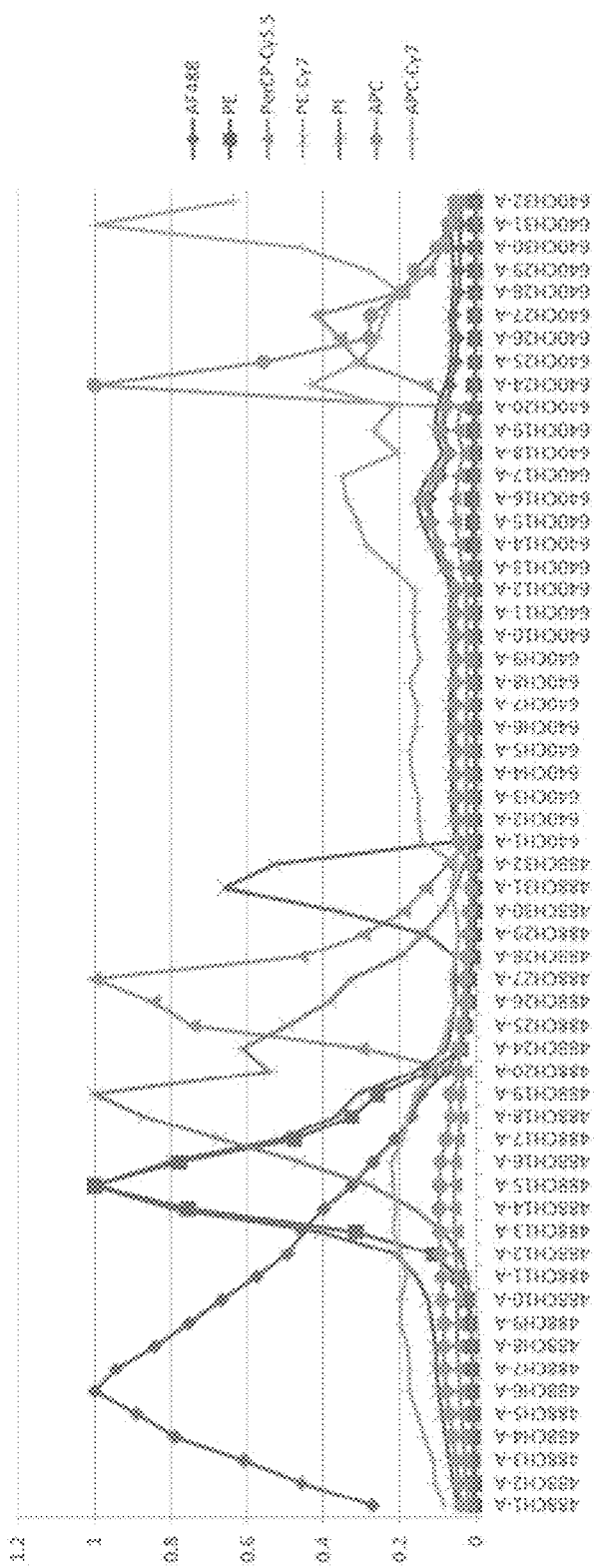
FIG. 7 is a spectrogram showing an example of measured spectra in which invalid detected values are contained, respectively.

FIG. 7 shows an example of the measured spectra in each of which the invalid detected value(s) is(are) contained.

Graphs shown in FIG. 7 are obtained by measuring seven kinds of single-dyeing spectra about AF488, PE, PerCP-Cy5.5, PE-Cy7, PI, APC, and APC-Cy7. In this case, the seven kinds of single-dyeing spectra are all normalized so that each of their peaks becomes 1. In FIG. 7, the axis of abscissa represents PMT, and the axis of ordinate represents the detected value. Also, the detected values of the fluorescence spectrum obtained by excitation made by radiation of a 488 nm-laser beam are indicated in 488Ch1 to 488Ch32, and the detected values of the fluorescence spectrum obtained by excitation made by radiation of a 640 nm-laser beam are indicated in 640Ch1 to 640Ch32.

Figure 8:
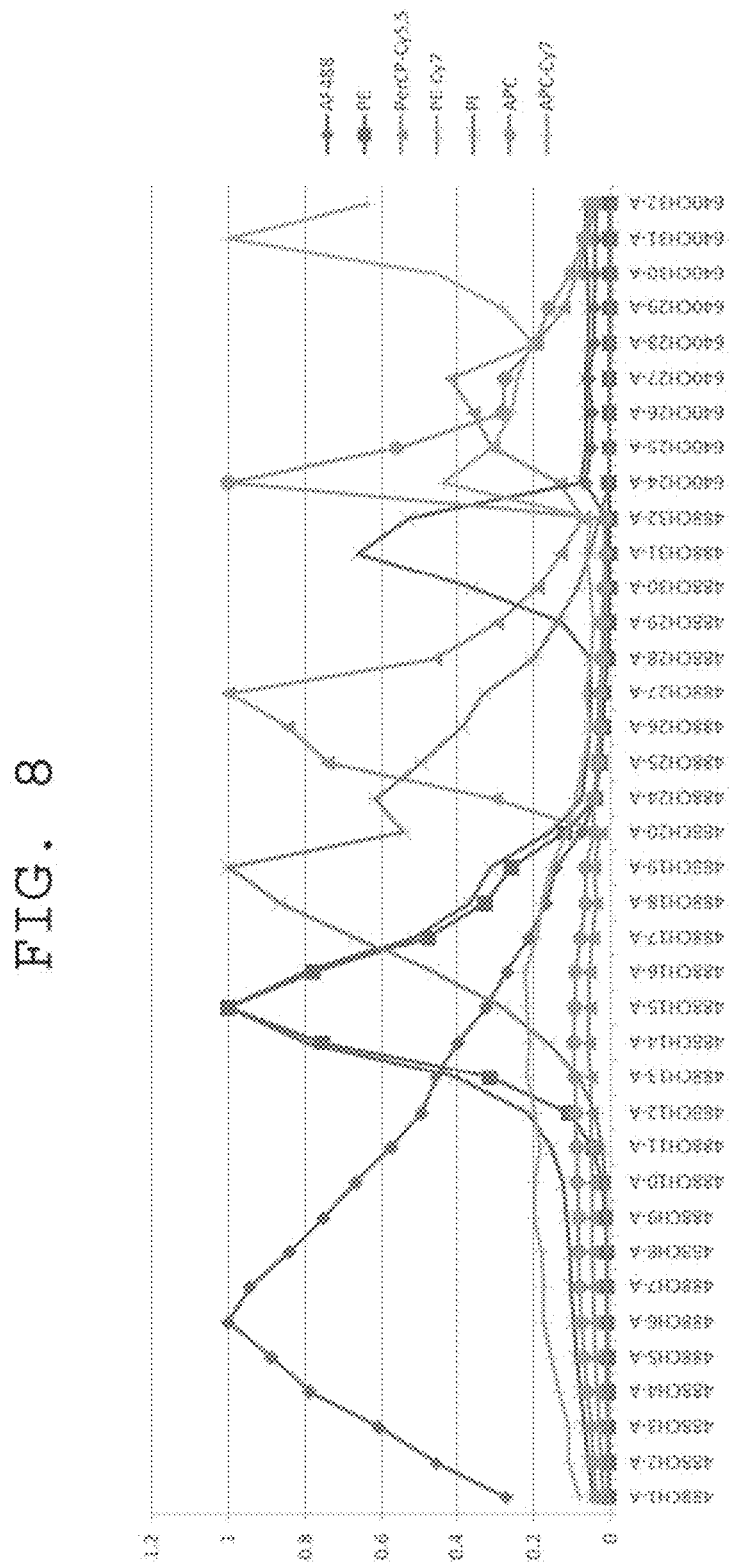
FIG. 8 is a spectrogram showing spectra obtained by excluding the invalid detected values from the measured spectra shown in FIG. 7.
Figure 9A:
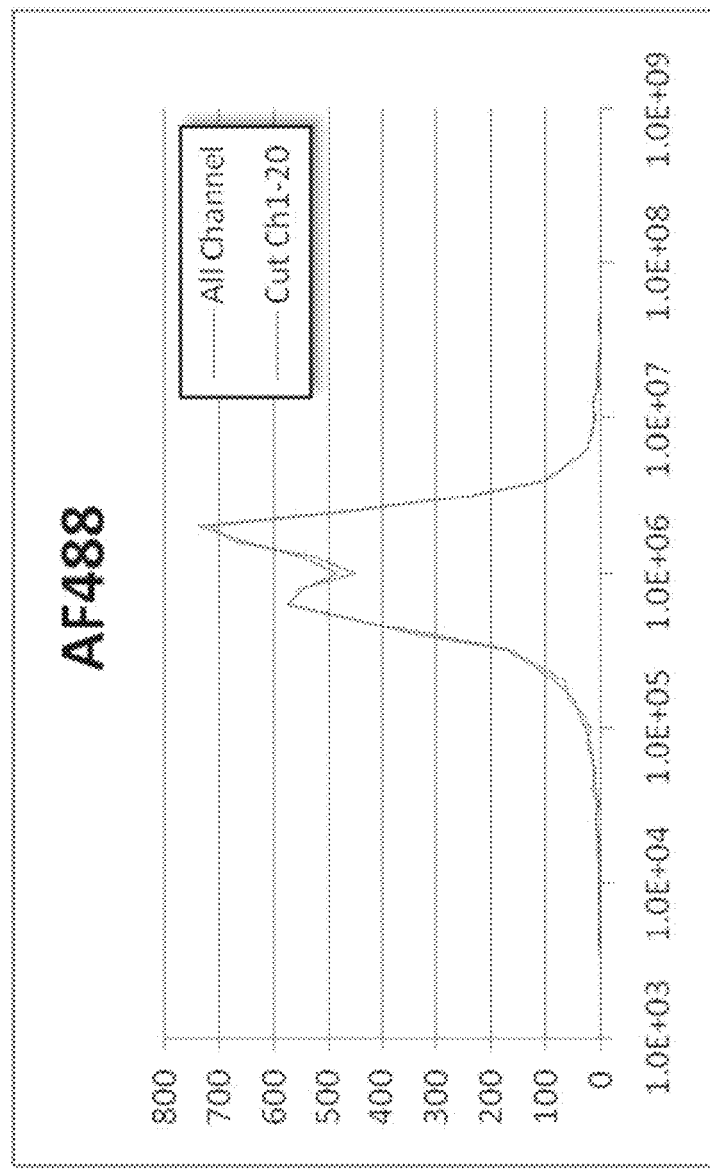
FIGS. 9A-9G are diagrams showing results obtained by subjecting the spectra shown in FIGS. 7 and 8 to the fluorescence correcting processing by using a method utilizing a least-squares method in the present embodiment, thereby comparing right and wrong of separation with each other.
Figure 9B:
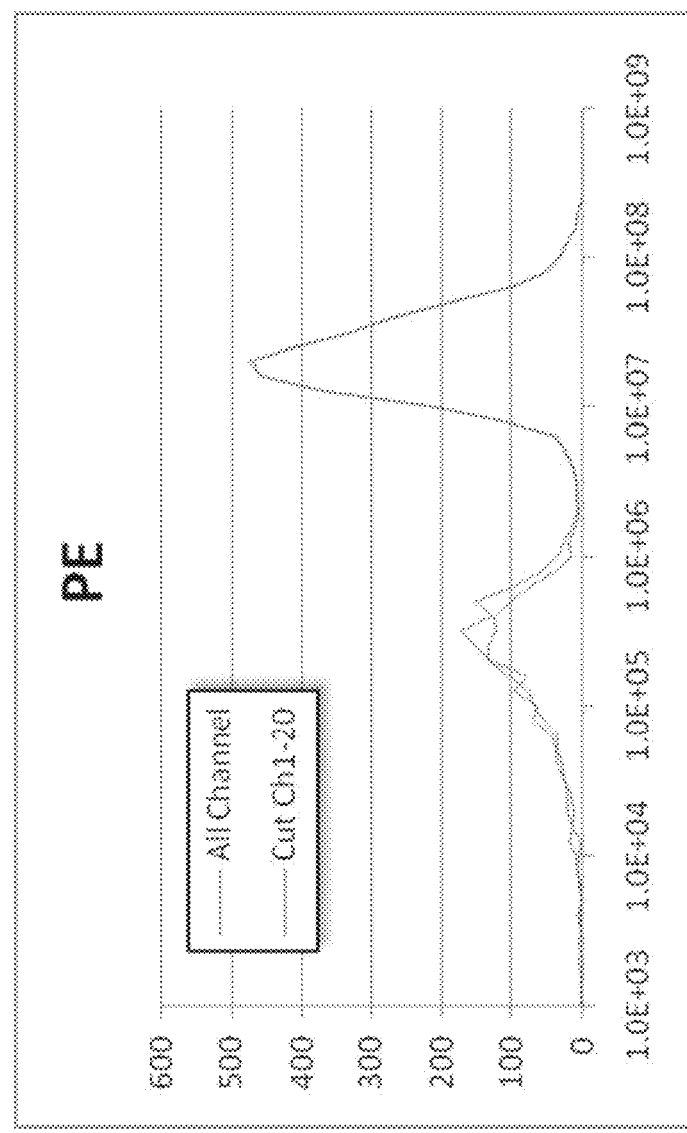
Figure 9C:
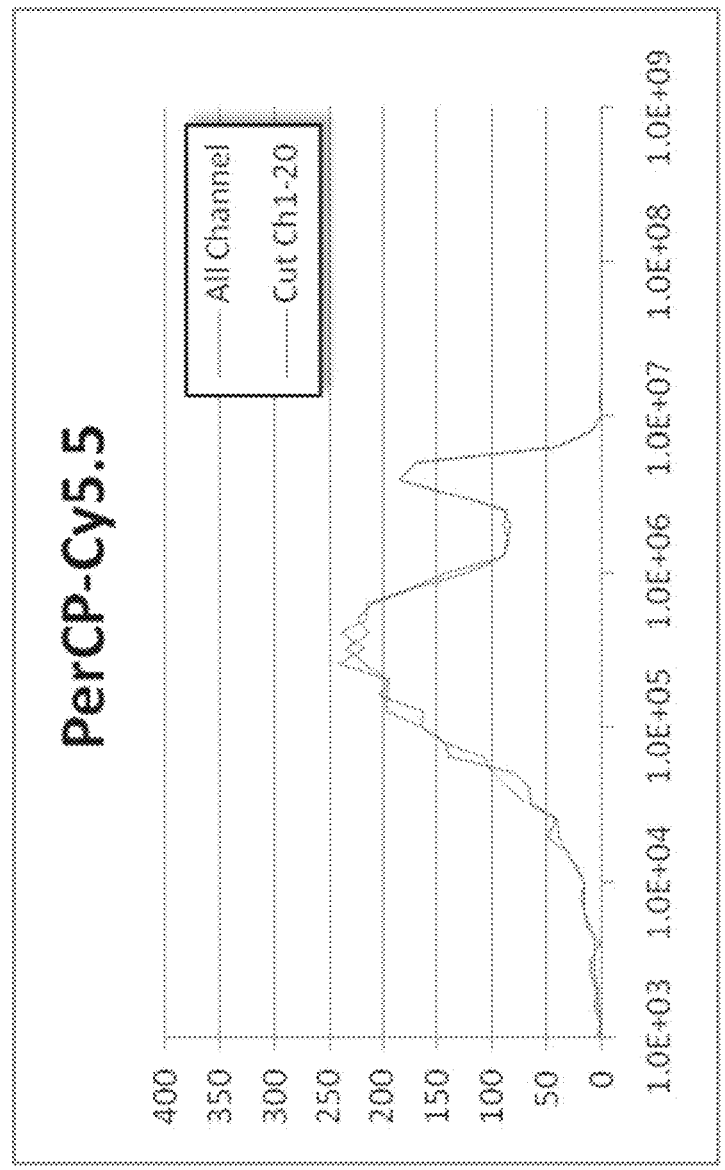
Figure 9D:
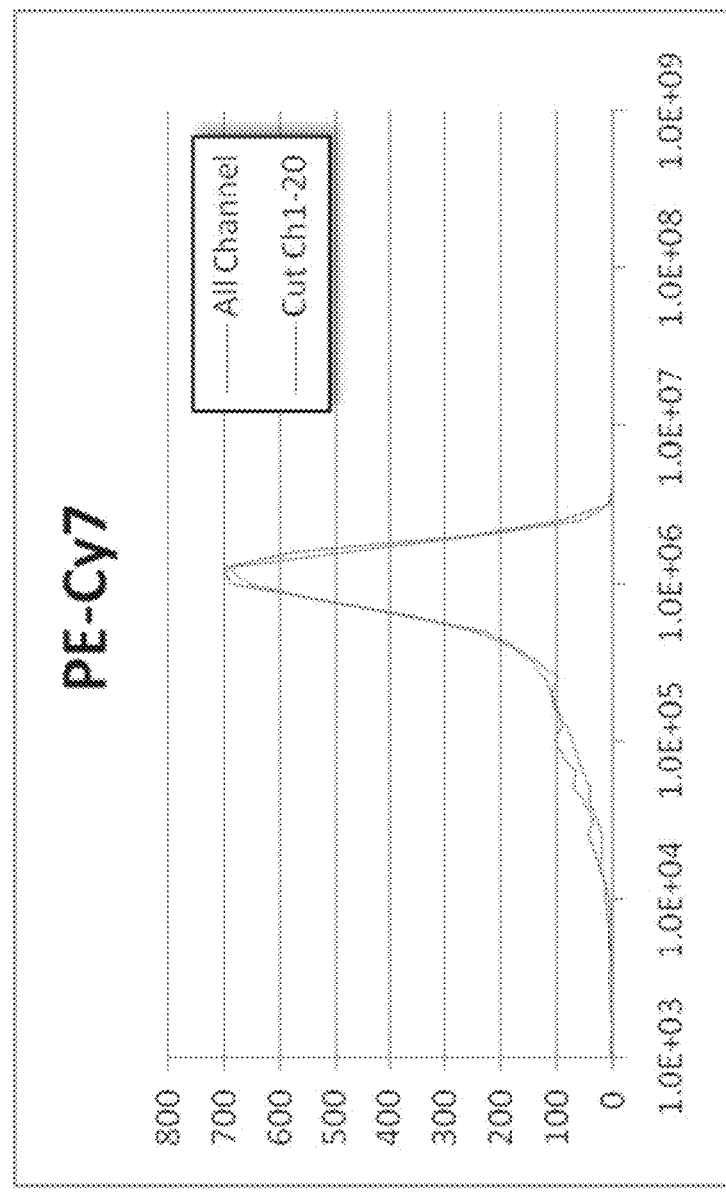
Figure 9E:
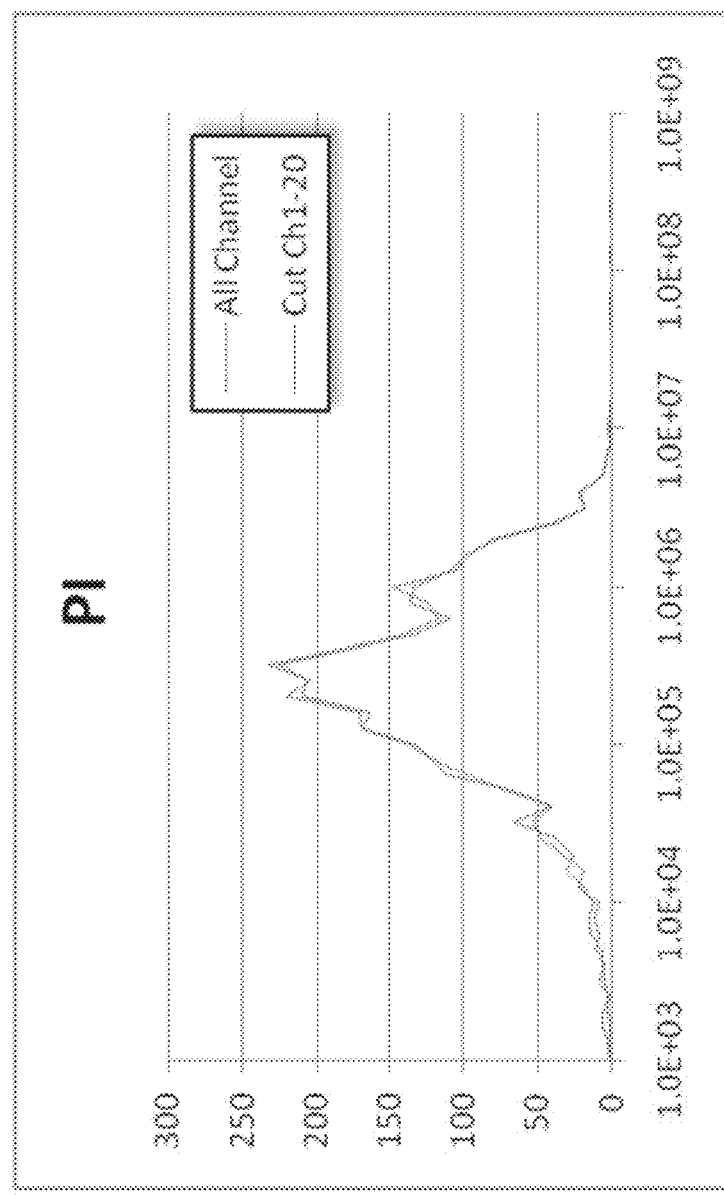
Figure 9F:
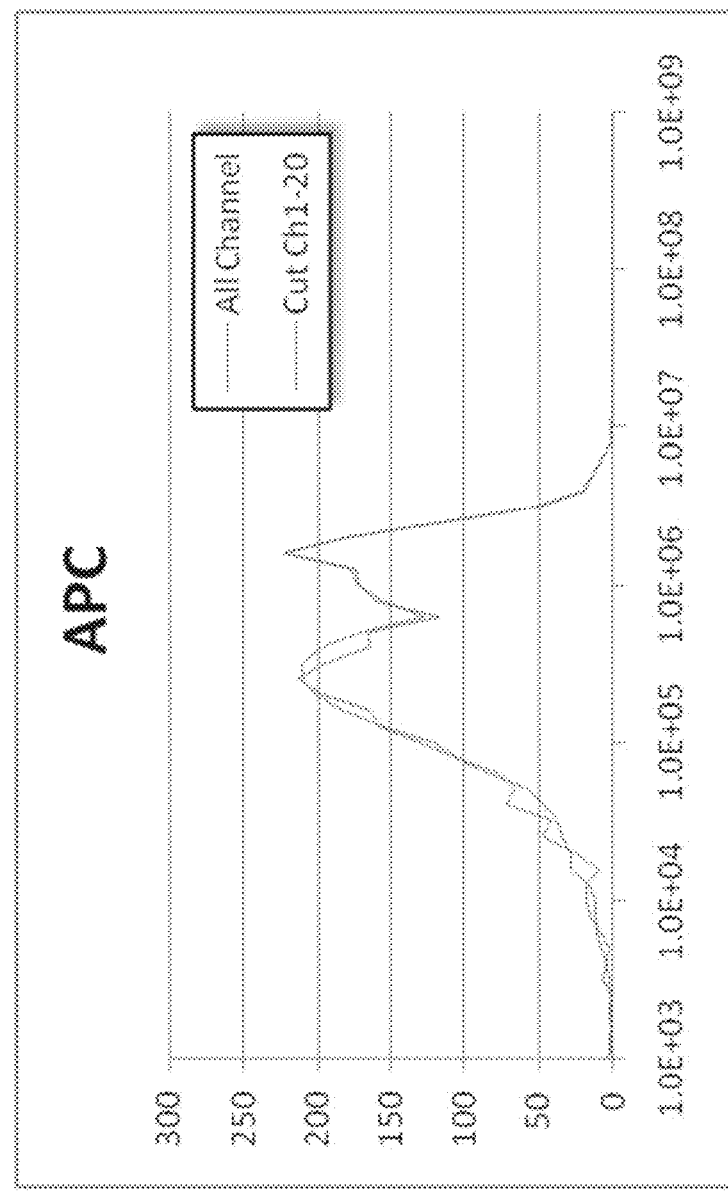
Figure 9G:
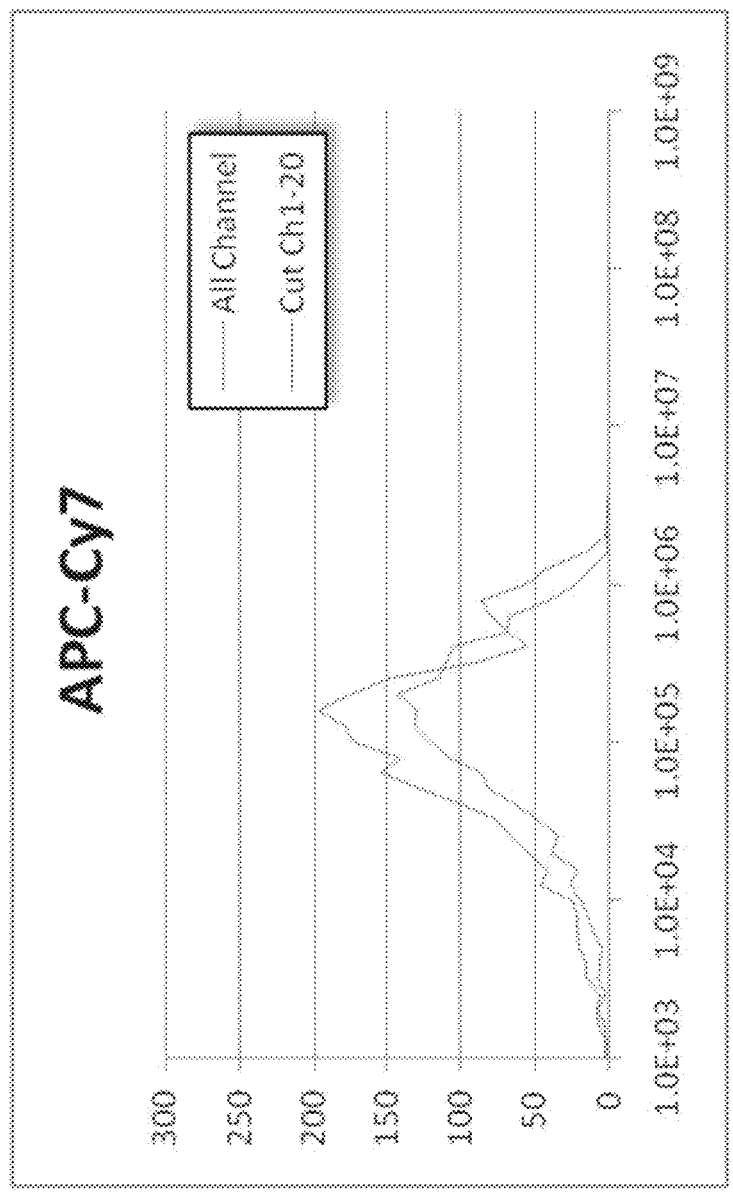

Although with regard to the fluorescent dye excited by radiation of the 640 nm-laser beam, there are PerCP-Cy5.5, PE-Cy7, APC, and APC-Cy7, it is known that any of those fluorescent dyes does not generate the fluorescence with the wavelengths sensed by the detectors 640Ch1 to 640Ch20 in theory. In addition, any of AF488, PE and PI is not excited at all by radiation of the 640 nm-laser beam. Therefore, the wavelengths appearing in 640Ch1 to 640Ch20 are the noises and thus are the invalid detected values. FIG. 8 shows spectra in each of which these invalid detected values are excluded.

FIGS. 9A-9G are diagrams showing results obtained by processing the spectra shown in FIGS. 7 and 8 by using the fluorescence intensity correcting method utilizing the least-squares method, thereby comparing right and wrong of the separation. In FIGS. 9A-9G, "All Channel" represents the results obtained by processing the measured data in which the invalid detected values are contained. Also, "Cut Ch1-20" represents the results obtained by processing the data from which the invalid detected values are excluded. It is understood that the detected values, indicated by 640Ch1 to 640Ch20, as the invalid detected values are excluded from the measured data, whereby in particular, the separation of APC-Cy7 becomes good.

According to the fluorescence intensity correcting method, the fluorescence intensity calculating method, and the fluorescence intensity calculating apparatus of the present embodiment, when the microparticle labeled with the plural fluorescent dyes is multicolor-measured by using the plural photodetectors, the measured data obtained from all the photodetectors is effectively utilized without depending on the number of fluorescent dyes, thereby making it possible to precisely calculate the fluorescence intensities from the respective fluorescent dyes. Therefore, the fluorescence intensity correcting method, the fluorescence intensity calculating method, and the fluorescence intensity calculating apparatus of the present embodiment can contribute to that the characteristics of the microparticle such as cell are more minutely analyzed.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The invention claimed is:

1. A microparticle processing method, comprising:
radiating a light in a range from 488 nm to 640 nm, by a laser light source in a cytometer apparatus, to a microparticle;
detecting, by photodetectors in the cytometer apparatus, multicolor measurements of fluorescences excited by the light;
receiving the multicolor measurements of the fluorescences, which are generated from plural fluorescent dyes excited by radiating the light to the microparticle, which is multiply-labeled with said plural fluorescent dyes by the photodetectors which correspond to different received light wavelength bands, respectively;
correcting fluorescence intensities of the multicolor measurements of the fluorescences in the cytometer apparatus by determining intensities of the multicolor measurements of the fluorescences generated from the fluorescent dyes by obtaining a parameter $a_k$ (k=1 to m) at which an evaluation function expressed by the following Expression gets a minimum value:

$$\chi^2 \equiv \sum_{i=1}^{N} \left[ \frac{y_i - \sum_{k=1}^{M} a_k X_k(x_i)}{\sigma_i} \right]^2$$

where $X_k(x_i)$ represents a detected value from the i-th photodetector in a single dyeing spectrum of the k-th fluorescent dye, wherein the single-dyeing spectrum is obtained from the microparticle individually labeled with the fluorescent dyes, $y_i$ represents a detected value from the i-th photodetector in the measured spectra, and $\sigma_i$ represents a reciprocal number of a weight for the measured value from the i-th photodetector; and
separating a plurality of microparticles into groups based on corrected fluorescence intensities.

2. The microparticle processing method according to claim 1, wherein the number of the photodetectors is larger than the number of the fluorescent dyes.

3. The microparticle processing method according to claim 1, wherein $\sigma_i$ represents a measurement error variance of the i-th photodetector as the reciprocal number of the weight.

4. The microparticle processing method according to claim 1, wherein at least one of $\sigma_i$ is set as 1.

5. The microparticle processing method according to claim 1, wherein in a case that a detected value from at least one photodetector in the measured spectra is an invalid value, the evaluation function is calculated by using the detected values other than the invalid detected value as $y_i$.

6. The microparticle processing method according to claim 1, wherein measured data obtained from all the photodetectors is effectively utilized without depending on a number of fluorescent dyes.

7. A microparticle processing method, comprising:
radiating a light in a range from 488 nm to 640 nm, by a laser light source in a cytometer apparatus, to a microparticle;
detecting, by photodetectors in the cytometer apparatus, multicolor measurements of fluorescences excited by the light;
receiving the multicolor measurements of the fluorescences, which are generated from plural fluorescent dyes excited by radiating the light to the microparticle, which is multiply-labeled with said plural fluorescent dyes by the photodetectors which correspond to different received light wavelength bands, respectively;
correcting fluorescence intensities of the multicolor measurements of the fluorescences in the cytometer apparatus by determining intensities of the fluorescences generated from the fluorescent dyes by obtaining a parameter $a_k$ (k=1 to m) at which an evaluation function expressed by the following Expression gets a minimum value:

$$X'_k(x_i) = X_k(x_i) \, (k = 1 \sim M_k \quad i = 1 \sim N_1)$$

$$X'_k(x_i) = 0 \, (k = 1 \sim M_k \quad i = N_1 + 1 \sim N)$$

$$\chi^2 \equiv \sum_{i=1}^{N} \left[ \frac{y_i - \sum_{k=1}^{M} a_k X_k(x_i)}{\sigma_i} \right]^2$$

where $X_k(x_i)$ represents a detected value from the i-th photodetector in a single-dyeing spectrum of the k-th fluorescent dye, wherein the single-dyeing spectrum is obtained from the microparticle individually labeled with the fluorescent dyes, $y_i$ represents a detected value from the i-th photodetector in the measured spectra, $\sigma_i$ represents a reciprocal number of a weight for the measured value from the i-th photodetector, an invalid detected value is taken to be $y_i$ (i="$N_1+1$" to N), and a valid detected value is taken to be $y_i$ (i=1 to $N_1$); and separating a plurality of microparticles into groups based on corrected fluorescence intensities.

8. The microparticle processing method according to claim 7, wherein the number of the photodetectors is larger than the number of the fluorescent dyes.

9. The microparticle processing method according to claim 7, wherein $\sigma_i$ represents a measurement error variance of the i-th photodetector as the reciprocal number of the weight.

10. The microparticle processing method according to claim 7, wherein measured data obtained from all the photodetectors is effectively utilized without depending on a number of fluorescent dyes.

11. A microparticle processing apparatus, comprising:
a laser light source in a cytometer apparatus configured to radiate a light in a range from 488 nm to 640 nm to a microparticle;
photodetectors in the cytometer apparatus, multicolor measurements of configured to detect fluorescences excited by the light; and
a data processing device that includes circuitry configured to:
receive the multicolor measurements of the fluorescences, which are generated from plural fluorescent dyes excited by the laser light source radiating the light to the microparticle, which is multiply-labeled with said plural fluorescent dyes by the photodetectors which correspond to different received light wavelength bands, respectively;

correct fluorescence intensities of the multicolor measurements of the fluorescences in the cytometer apparatus by determine intensities of the fluorescences generated from the fluorescent dyes by obtaining a parameter $a_k$ (k=1 to m) at which an evaluation function expressed by the following Expression gets a minimum value:

$$\chi^2 \equiv \sum_{i=1}^{N} \left[ \frac{y_i - \sum_{k=1}^{M} a_k X_k(x_i)}{\sigma_i} \right]^2$$

where $X_k(x_i)$ represents a detected value from the i-th photodetector in a single dyeing spectrum of the k-th fluorescent dye, wherein the single-dyeing spectrum is obtained from the microparticle individually labeled with the fluorescent dyes, $y_i$ represents a detected value from the i-th photodetector in the measured spectra, and $\sigma_i$ represents a reciprocal number of a weight for the measured value from the i-th photodetector; and separate a plurality of microparticles into groups based on corrected fluorescence intensities.

12. The microparticle processing apparatus according to claim 11, wherein the fluorescence intensity calculating apparatus is flow cytometer.

13. The microparticle processing apparatus according to claim 11, wherein the number of the photodetectors is larger than the number of the fluorescent dyes.

14. The microparticle processing apparatus according to claim 11, wherein $\sigma_i$ represents a measurement error variance of the i-th photodetector as the reciprocal number of the weight.

15. The microparticle processing apparatus according to claim 11, wherein measured data obtained from all the photodetectors is effectively utilized without depending on a number of fluorescent dyes.

* * * * *